(12) United States Patent
Azagury et al.

(10) Patent No.: US 9,770,194 B2
(45) Date of Patent: Sep. 26, 2017

(54) DEVICES AND METHODS FOR AIRWAY MEASUREMENT

(71) Applicant: Ciel Medical, Inc., Redwood City, CA (US)

(72) Inventors: Dan E. Azagury, Palo Alto, CA (US); Mary K. Garrett, Redwood City, CA (US); Ronan L. Jenkinson, Pittsburg, CA (US); Henry Lao, Milpitas, CA (US); Gary B. Hulme, San Jose, CA (US); Jacqueline Rose, Carmichael, CA (US); Casey Landey, San Francisco, CA (US)

(73) Assignee: Ciel Medical, Inc., Redwood City, CA (US)

( * ) Notice: Subject to any disclaimer, the term of this patent is extended or adjusted under 35 U.S.C. 154(b) by 0 days.

(21) Appl. No.: 14/534,084

(22) Filed: Nov. 5, 2014

(65) Prior Publication Data

US 2015/0126908 A1 May 7, 2015

Related U.S. Application Data

(60) Provisional application No. 61/900,361, filed on Nov. 5, 2013, provisional application No. 61/938,642, filed
(Continued)

(51) Int. Cl.
*A61B 5/107* (2006.01)
*A61M 16/04* (2006.01)

(52) U.S. Cl.
CPC ....... *A61B 5/1076* (2013.01); *A61M 16/0488* (2013.01)

(58) Field of Classification Search
CPC .......... A61M 16/0833; A61M 16/0486; A61M 16/0488; A61M 16/0418; A61M 16/0484;
(Continued)

(56) References Cited

U.S. PATENT DOCUMENTS 2,463,149 A 3/1949 Caine
2,541,402 A 2/1951 Caine
(Continued)

FOREIGN PATENT DOCUMENTS

EP 0900048 A1 3/1999
EP 1767182 A1 3/2007
(Continued)

OTHER PUBLICATIONS

International Search Report and Written Opinion received for PCT Patent Application No. PCT/US2014/064179 mailed on Feb. 18, 2015, 9 pages.
(Continued)

*Primary Examiner* — Rene Towa
(74) *Attorney, Agent, or Firm* — McDermott Will & Emery LLP

(57) ABSTRACT

Described here are devices and methods for measuring a distance in an airway. In some instances, the devices may comprise an outer shaft and an inner shaft that is slidably disposed in a lumen of the outer shaft. An expandable stopper may be positioned at a distal end of the inner shaft, which may be configured to engage a carina of a patient. The device may comprise one or more alignment markings and one or more displacement markings that may be used to measure a distance between a distal tip of an endotracheal tube and the carina. In some variations, measurement may be facilitated by the use of an alignment guide that may attach to a predetermined portion of an endotracheal tube.

18 Claims, 27 Drawing Sheets

Related U.S. Application Data on Feb. 11, 2014, provisional application No. 62/006,405, filed on Jun. 2, 2014, provisional application No. 62/061,109, filed on Oct. 7, 2014.

(58) Field of Classification Search
CPC .......... A61M 16/0816; A61M 16/0434; A61M 25/0097; A61M 25/0032; A61M 25/04; A61M 25/0041; A61M 2025/0175; A61M 2025/0037; A61M 2025/583; A61M 2205/6045; A61M 2205/3375; A61M 2205/32

See application file for complete search history.

(56) References Cited

U.S. PATENT DOCUMENTS

| | | | |
|---|---|---|---|
| 3,516,408 | A | 6/1970 | Montanti |
| 3,538,918 | A | 11/1970 | Engelsher et al. |
| 3,760,811 | A | 9/1973 | Andrew |
| 3,792,701 | A | 2/1974 | Kloz et al. |
| 3,799,173 | A | 3/1974 | Kamen |
| 3,827,437 | A | 8/1974 | Inaba |
| 4,043,346 | A | 8/1977 | Mobley et al. |
| 4,244,362 | A | 1/1981 | Anderson |
| 4,256,099 | A | 3/1981 | Dryden |
| 4,273,128 | A | 6/1981 | Lary |
| 4,289,128 | A | 9/1981 | Rusch |
| 4,309,994 | A | 1/1982 | Grunwald |
| 4,344,436 | A | 8/1982 | Kubota |
| 4,393,872 | A | 7/1983 | Reznik et al. |
| 4,416,273 | A | 11/1983 | Grimes |
| 4,416,289 | A | 11/1983 | Bresler |
| 4,431,005 | A | 2/1984 | McCormick |
| 4,445,501 | A | 5/1984 | Bresler |
| 4,447,227 | A | 5/1984 | Kotsanis |
| 4,449,522 | A | 5/1984 | Baum |
| 4,453,545 | A | 6/1984 | Inoue |
| 4,502,482 | A | 3/1985 | DeLuccia et al. |
| 4,567,882 | A | 2/1986 | Heller |
| 4,633,864 | A | 1/1987 | Walsh |
| 4,646,733 | A | 3/1987 | Stroh et al. |
| 4,658,818 | A | 4/1987 | Miller, Jr. et al. |
| 4,685,457 | A | 8/1987 | Donenfeld |
| 4,690,138 | A | 9/1987 | Heyden |
| 4,712,551 | A | 12/1987 | Rayhanabad |
| 4,787,399 | A | 11/1988 | Bonello et al. |
| 4,819,664 | A * | 4/1989 | Nazari .................... 128/207.15 |
| 4,827,925 | A | 5/1989 | Vilasi |
| 4,840,172 | A * | 6/1989 | Augustine et al. ...... 128/207.14 |
| 4,848,331 | A | 7/1989 | Northway-Meyer |
| 4,881,542 | A | 11/1989 | Schmidt et al. |
| 4,896,667 | A | 1/1990 | Magnuson et al. |
| 4,943,770 | A | 7/1990 | Ashley-Rollman et al. |
| 4,949,716 | A | 8/1990 | Chenoweth |
| 4,960,122 | A | 10/1990 | Mizus |
| 4,967,744 | A | 11/1990 | Chua |
| 4,969,878 | A | 11/1990 | Schmidt et al. |
| 4,976,261 | A | 12/1990 | Gluck et al. |
| 4,995,878 | A | 2/1991 | Rai |
| 5,003,963 | A | 4/1991 | Bullard et al. |
| 5,009,227 | A | 4/1991 | Nieuwstad |
| 5,010,892 | A | 4/1991 | Colvin et al. |
| 5,031,613 | A | 7/1991 | Smith et al. |
| 5,038,766 | A | 8/1991 | Parker |
| 5,042,469 | A | 8/1991 | Augustine |
| 5,080,104 | A | 1/1992 | Marks et al. |
| 5,095,896 | A | 3/1992 | Omoigui |
| 5,099,845 | A | 3/1992 | Besz et al. |
| 5,135,490 | A | 8/1992 | Strickland |
| 5,158,569 | A | 10/1992 | Strickland et al. |
| 5,163,941 | A | 11/1992 | Garth et al. |
| 5,165,420 | A | 11/1992 | Strickland |
| 5,174,283 | A | 12/1992 | Parker |
| 5,193,544 | A | 3/1993 | Jaffe |
| 5,199,427 | A | 4/1993 | Strickland |
| 5,203,320 | A | 4/1993 | Augustine |
| 5,218,957 | A | 6/1993 | Strickland |
| 5,230,332 | A | 7/1993 | Strickland |
| 5,231,983 | A | 8/1993 | Matson et al. |
| 5,235,970 | A | 8/1993 | Augustine |
| 5,242,389 | A | 9/1993 | Schrader et al. |
| 5,246,012 | A | 9/1993 | Strickland |
| 5,259,371 | A * | 11/1993 | Tonrey .................... 128/200.26 |
| 5,259,377 | A | 11/1993 | Schroeder |
| 5,263,478 | A * | 11/1993 | Davis ...................... 128/207.14 |
| 5,273,534 | A | 12/1993 | Knoepfler |
| 5,285,778 | A | 2/1994 | Mackin |
| 5,316,024 | A | 5/1994 | Hirschi et al. |
| 5,329,940 | A | 7/1994 | Adair |
| 5,331,967 | A | 7/1994 | Akerson |
| 5,339,805 | A | 8/1994 | Parker |
| 5,359,999 | A | 11/1994 | Kinsman |
| 5,383,467 | A | 1/1995 | Auer et al. |
| 5,386,828 | A | 2/1995 | Owens et al. |
| 5,400,771 | A | 3/1995 | Pirak et al. |
| 5,405,325 | A | 4/1995 | Labs |
| 5,425,370 | A | 6/1995 | Vilkomerson |
| 5,425,382 | A | 6/1995 | Golden et al. |
| 5,445,144 | A | 8/1995 | Wodicka et al. |
| 5,445,161 | A | 8/1995 | Huang |
| 5,464,409 | A * | 11/1995 | Mohajer ...................... 606/119 |
| 5,520,697 | A * | 5/1996 | Lindenberg et al. ......... 606/108 |
| 5,551,946 | A | 9/1996 | Bullard |
| 5,560,351 | A | 10/1996 | Gravenstein et al. |
| 5,588,424 | A | 12/1996 | Insler et al. |
| 5,622,169 | A | 4/1997 | Golden et al. |
| 5,626,128 | A | 5/1997 | Bradley et al. |
| 5,642,730 | A | 7/1997 | Baran |
| 5,645,065 | A | 7/1997 | Shapiro et al. |
| 5,660,175 | A | 8/1997 | Dayal |
| 5,665,052 | A | 9/1997 | Bullard |
| 5,669,924 | A | 9/1997 | Shaknovich |
| 5,672,179 | A | 9/1997 | Garth et al. |
| 5,701,918 | A | 12/1997 | Jiraki |
| 5,720,735 | A | 2/1998 | Dorros |
| 5,743,254 | A | 4/1998 | Parker |
| 5,775,322 | A | 7/1998 | Silverstein et al. |
| 5,785,051 | A | 7/1998 | Lipscher et al. |
| 5,791,338 | A | 8/1998 | Merchant et al. |
| 5,800,342 | A | 9/1998 | Lee et al. |
| 5,803,898 | A | 9/1998 | Bashour |
| 5,840,013 | A | 11/1998 | Lee et al. |
| 5,842,973 | A | 12/1998 | Bullard |
| 5,853,004 | A | 12/1998 | Goodman |
| 5,879,297 | A | 3/1999 | Haynor et al. |
| 5,902,238 | A | 5/1999 | Golden et al. |
| 5,913,816 | A | 6/1999 | Sanders et al. |
| 5,921,926 | A | 7/1999 | Rolland et al. |
| 5,954,636 | A | 9/1999 | Schwartz et al. |
| 5,975,697 | A | 11/1999 | Podoleanu et al. |
| 5,996,582 | A | 12/1999 | Turnbull |
| 6,063,022 | A | 5/2000 | Ben-Haim |
| 6,079,413 | A | 6/2000 | Baran |
| 6,129,668 | A | 10/2000 | Haynor et al. |
| 6,132,379 | A | 10/2000 | Patacsil et al. |
| 6,142,144 | A | 11/2000 | Pacey |
| 6,161,537 | A | 12/2000 | Gravenstein et al. |
| 6,164,277 | A | 12/2000 | Merideth |
| 6,202,646 | B1 | 3/2001 | Camodeca et al. |
| 6,216,028 | B1 | 4/2001 | Haynor et al. |
| 6,253,770 | B1 | 7/2001 | Acker et al. |
| 6,254,591 | B1 | 7/2001 | Roberson |
| 6,263,230 | B1 | 7/2001 | Haynor et al. |
| 6,280,464 | B1 * | 8/2001 | Hayashi ...................... 623/1.11 |
| 6,332,089 | B1 | 12/2001 | Acker et al. |
| 6,349,720 | B1 | 2/2002 | Clark |
| 6,378,521 | B1 | 4/2002 | Van Den Berg |
| 6,415,787 | B1 | 7/2002 | Boussignac |
| 6,443,156 | B1 | 9/2002 | Niklason et al. |
| 6,453,190 | B1 | 9/2002 | Acker et al. |
| 6,463,927 | B1 | 10/2002 | Pagan |
| 6,513,527 | B1 | 2/2003 | Abdel-Aziz |
| 6,517,492 | B2 * | 2/2003 | Koblanski ............ A61B 5/0205 600/481 |

(56) References Cited

U.S. PATENT DOCUMENTS

| | | |
|---|---|---|
| 6,536,437 B1 | 3/2003 | Dragisic |
| 6,609,521 B1 | 8/2003 | Belani et al. |
| 6,634,360 B1 | 10/2003 | Flodin |
| 6,637,435 B2 | 10/2003 | Ciaglia et al. |
| 6,660,001 B2 | 12/2003 | Gregory |
| 6,668,198 B2 | 12/2003 | Swanson et al. |
| 6,668,832 B2 | 12/2003 | Hipolito et al. |
| 6,672,305 B2 | 1/2004 | Parker |
| 6,672,308 B1 | 1/2004 | Gaspari |
| 6,698,424 B2 | 3/2004 | Madsen et al. |
| 6,705,319 B1 | 3/2004 | Wodicka et al. |
| 6,729,334 B1 | 5/2004 | Baran |
| 6,761,693 B1 | 7/2004 | Rasmussen |
| 6,789,538 B2 | 9/2004 | Wright et al. |
| 6,820,614 B2 | 11/2004 | Bonutti |
| 6,860,264 B2 | 3/2005 | Christopher |
| 6,889,693 B2 | 5/2005 | Hipolito et al. |
| 6,978,784 B2 | 12/2005 | Pekar |
| 7,013,890 B2 | 3/2006 | Wakabayashi |
| 7,089,928 B2 | 8/2006 | Besharim et al. |
| 7,124,755 B2 | 10/2006 | Van Hooser |
| 7,147,252 B2 | 12/2006 | Teuscher et al. |
| 7,179,220 B2 | 2/2007 | Kukuk |
| RE39,508 E | 3/2007 | Parker |
| 7,258,120 B2 | 8/2007 | Melker |
| 7,320,319 B2 | 1/2008 | Bonutti |
| 7,469,700 B2 | 12/2008 | Baran |
| 7,472,705 B2 | 1/2009 | Baran |
| 7,516,741 B2 | 4/2009 | Glusker et al. |
| 7,552,729 B2 | 6/2009 | O'Mara |
| 7,585,836 B2 | 9/2009 | Goodson, IV et al. |
| 7,691,397 B2 | 4/2010 | Brown et al. |
| 7,766,961 B2 | 8/2010 | Patel et al. |
| 7,771,401 B2 | 8/2010 | Hekmat et al. |
| 7,900,634 B2 | 3/2011 | Tjong Joe Wai |
| 7,913,693 B2 | 3/2011 | Nelson et al. |
| 7,914,503 B2 | 3/2011 | Goodson, IV et al. |
| 7,914,517 B2 | 3/2011 | Baran et al. |
| 7,921,847 B2 | 4/2011 | Totz |
| 7,925,339 B2 | 4/2011 | Wik |
| 7,950,393 B2 | 5/2011 | Colburn et al. |
| 7,975,700 B2 | 7/2011 | Frazier et al. |
| 7,992,562 B2 | 8/2011 | Chen |
| 7,992,567 B2 | 8/2011 | Hirotsuka et al. |
| 7,993,325 B2 | 8/2011 | Elkins et al. |
| 7,997,266 B2 | 8/2011 | Frazier et al. |
| 8,006,697 B2 | 8/2011 | Boussignac |
| 8,010,180 B2 | 8/2011 | Quaid et al. |
| 8,012,121 B2 | 9/2011 | Goodson, IV et al. |
| 8,096,303 B2 | 1/2012 | Dineen et al. |
| 8,116,858 B2 | 2/2012 | Koblanski |
| 8,189,886 B2 | 5/2012 | Huo et al. |
| 8,196,584 B2 | 6/2012 | Maguire et al. |
| 8,231,524 B2 | 7/2012 | Schwartz et al. |
| 8,244,329 B2 | 8/2012 | Su |
| 8,280,489 B2 | 10/2012 | Li et al. |
| 8,307,830 B2 | 11/2012 | Clayton |
| 8,336,541 B2 | 12/2012 | Schwartz et al. |
| 8,371,307 B2 | 2/2013 | Hirotsuka et al. |
| 8,425,455 B2 | 4/2013 | Nentwick |
| 8,434,487 B2 | 5/2013 | Nelson et al. |
| 8,457,715 B2 | 6/2013 | McKenna et al. |
| 8,457,716 B2 | 6/2013 | Li et al. |
| 8,468,637 B2 | 6/2013 | Vazales et al. |
| 8,479,739 B2 | 7/2013 | Hirsh |
| 8,505,531 B2 | 8/2013 | Pecherer et al. |
| 8,518,011 B2 | 8/2013 | Goodson, IV et al. |
| 8,522,787 B2 | 9/2013 | Lin et al. |
| 8,577,108 B2 | 11/2013 | Huo et al. |
| 2002/0074002 A1 | 6/2002 | Tung et al. |
| 2002/0143380 A1 | 10/2002 | Dahl et al. |
| 2003/0121521 A1 | 7/2003 | Hipolito et al. |
| 2004/0035429 A1* | 2/2004 | Wakabayashi ........... 128/207.15 |
| 2004/0039252 A1 | 2/2004 | Koch, III |
| 2004/0221853 A1 | 11/2004 | Miller |
| 2005/0027215 A1* | 2/2005 | Baxter-Jones et al. ........ 600/591 |
| 2005/0038419 A9 | 2/2005 | Arnold et al. |
| 2005/0113701 A1 | 5/2005 | Chin et al. |
| 2005/0177024 A1 | 8/2005 | Mackin |
| 2006/0036164 A1 | 2/2006 | Wilson et al. |
| 2006/0064039 A1 | 3/2006 | Griego et al. |
| 2006/0081255 A1 | 4/2006 | Miller et al. |
| 2007/0137652 A1 | 6/2007 | Qureshi et al. |
| 2008/0039715 A1 | 2/2008 | Wilson et al. |
| 2008/0273209 A1 | 11/2008 | Delfyett |
| 2009/0024056 A1* | 1/2009 | Bacon ................. A61B 10/0233 600/567 |
| 2009/0143645 A1 | 6/2009 | Matthes |
| 2009/0171293 A1 | 7/2009 | Yang et al. |
| 2009/0209854 A1* | 8/2009 | Parihar et al. ................. 600/431 |
| 2010/0113519 A1 | 5/2010 | Kumar |
| 2010/0145192 A1 | 6/2010 | Elgort et al. |
| 2010/0179417 A1 | 7/2010 | Russo |
| 2010/0208270 A1 | 8/2010 | Kulkarni et al. |
| 2011/0031961 A1 | 2/2011 | Durand et al. |
| 2011/0098720 A1 | 4/2011 | Taylor et al. |
| 2013/0103163 A1 | 4/2013 | Krimsky et al. |
| 2013/0253310 A1 | 9/2013 | Mckenna et al. |
| 2014/0060655 A1* | 3/2014 | Ramos et al. .................... 137/1 |

FOREIGN PATENT DOCUMENTS

| | | |
|---|---|---|
| EP | 2517622 A2 | 10/2012 |
| EP | 2524713 A1 | 11/2012 |
| GB | 2098485 A | 11/1982 |
| SU | 124593 | 11/1959 |
| SU | 199338 | 9/1967 |
| SU | 908371 | 2/1982 |
| WO | 86/02564 A1 | 5/1986 |
| WO | 86/02848 A1 | 5/1986 |
| WO | 88/06903 A1 | 9/1988 |
| WO | 92/10971 A1 | 7/1992 |
| WO | 93/16752 A1 | 9/1993 |
| WO | 98/23317 A1 | 6/1998 |
| WO | 98/36684 A1 | 8/1998 |
| WO | 98/41272 A1 | 9/1998 |
| WO | 01/91843 A1 | 12/2001 |
| WO | 02/47748 A1 | 6/2002 |
| WO | 02/065903 A2 | 8/2002 |
| WO | 02/070038 A2 | 9/2002 |
| WO | 03/015610 A2 | 2/2003 |
| WO | 2006/018163 A2 | 2/2006 |
| WO | 2007/035297 A2 | 3/2007 |
| WO | 2007/088539 A2 | 8/2007 |
| WO | 2008/136658 A2 | 11/2008 |
| WO | 2009/026095 A1 | 2/2009 |
| WO | 2009/045378 A1 | 4/2009 |
| WO | 2009/099766 A2 | 8/2009 |
| WO | 2010/062603 A1 | 6/2010 |
| WO | 2010/091462 A1 | 8/2010 |
| WO | 2010/117999 A1 | 10/2010 |
| WO | 2010/118005 A1 | 10/2010 |
| WO | 2011/022802 A1 | 3/2011 |
| WO | 2012/138388 A1 | 10/2012 |
| WO | 2013/090619 A1 | 6/2013 |
| WO | 2013/118059 A1 | 8/2013 |

OTHER PUBLICATIONS

Extended European Search Report for Application No. 14860057.0, dated Jul. 13, 2017, 8 pages.

* cited by examiner

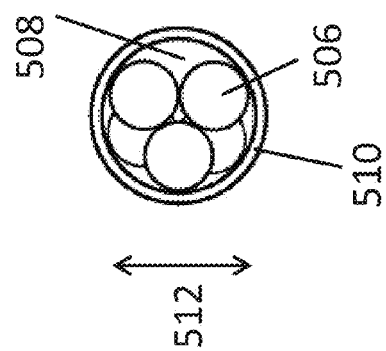
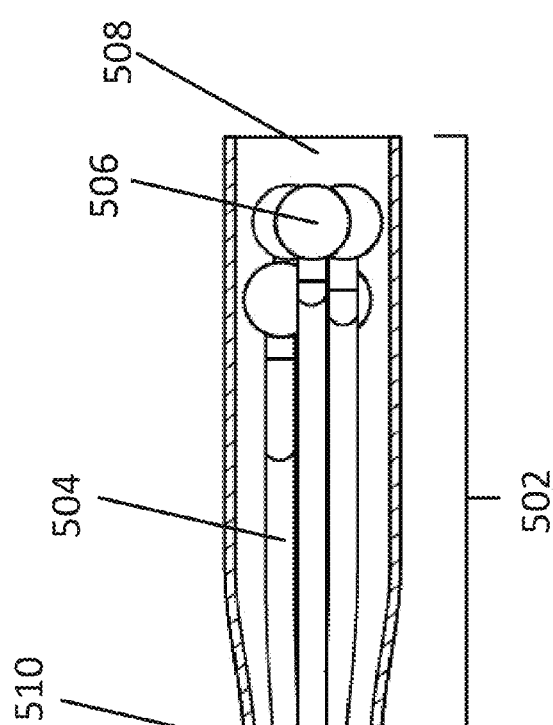
FIG. 5B
FIG. 5A

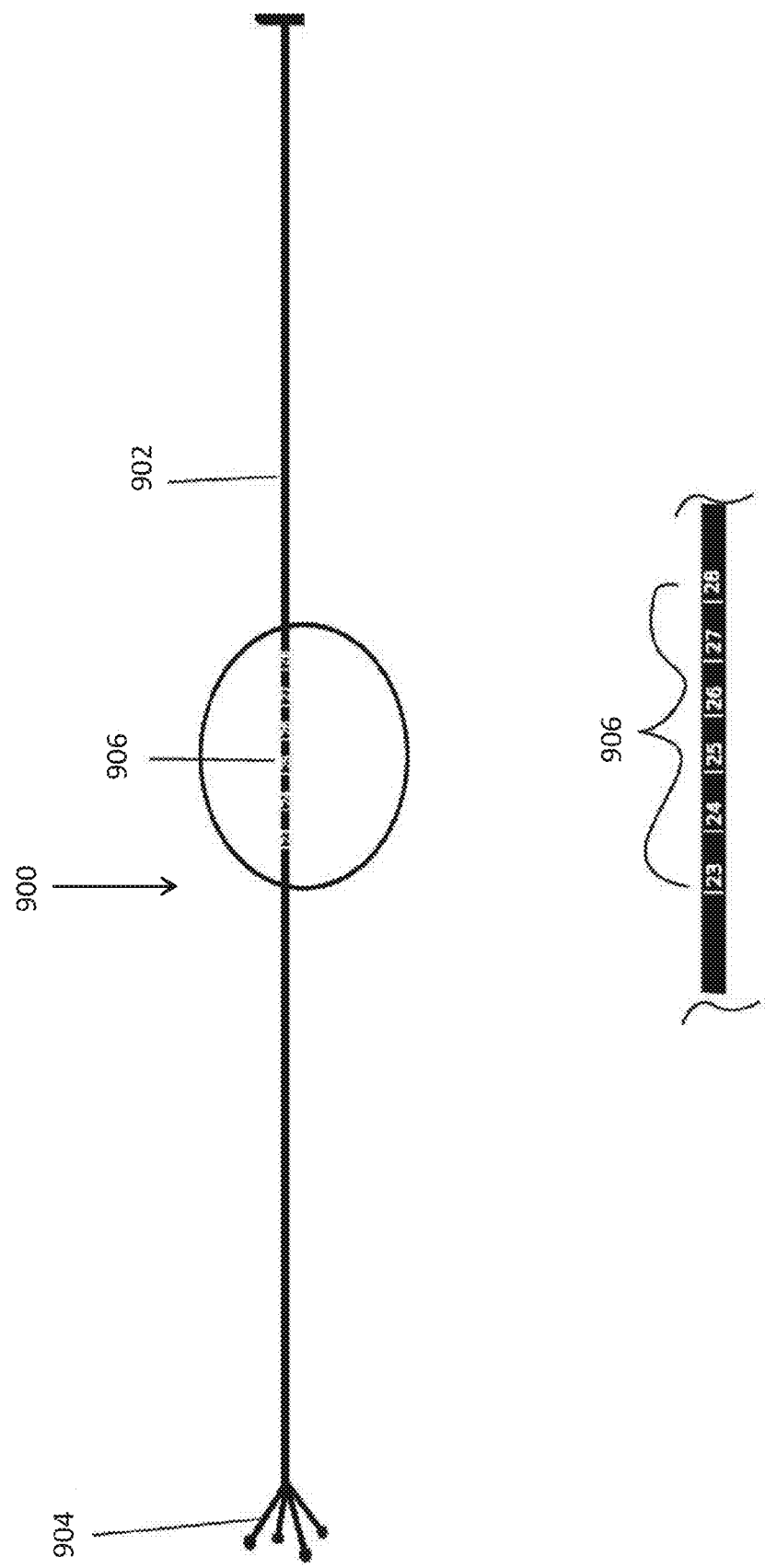

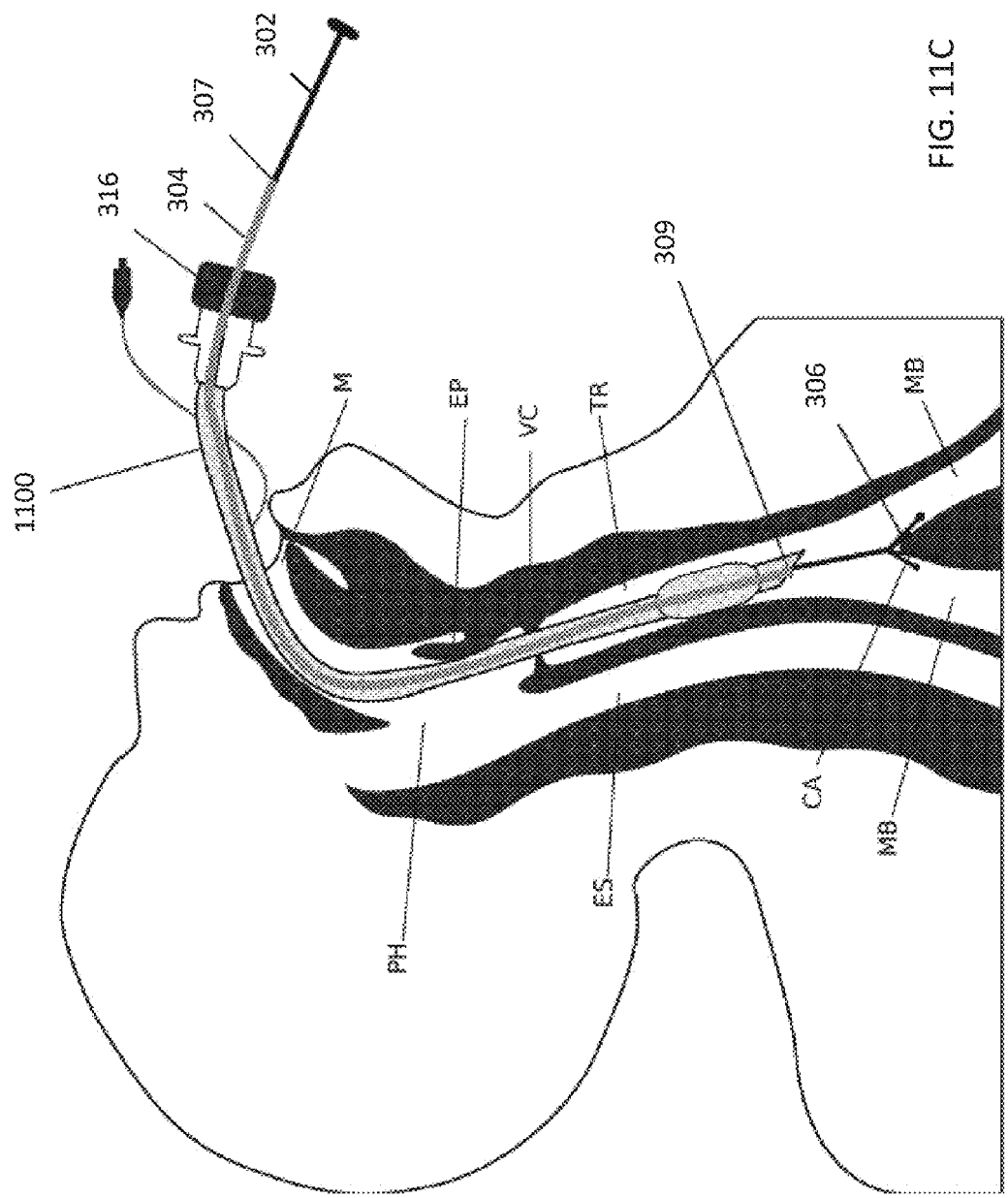

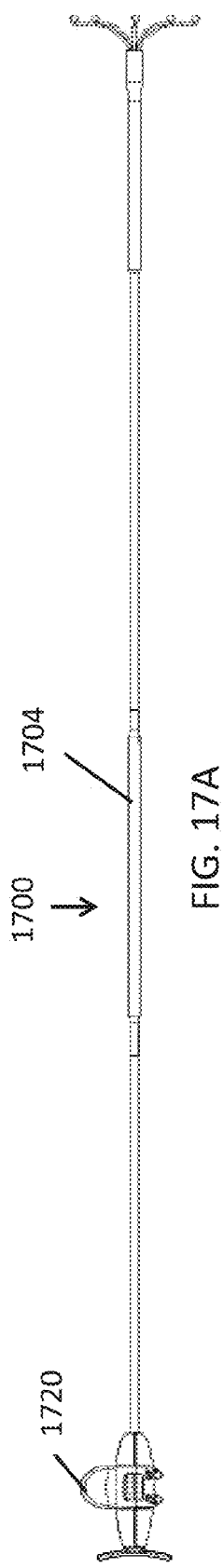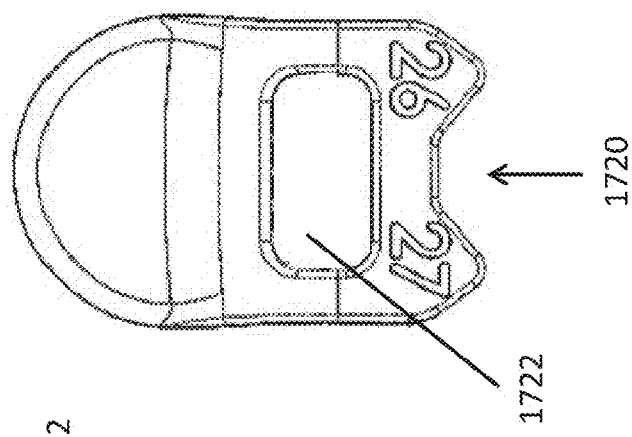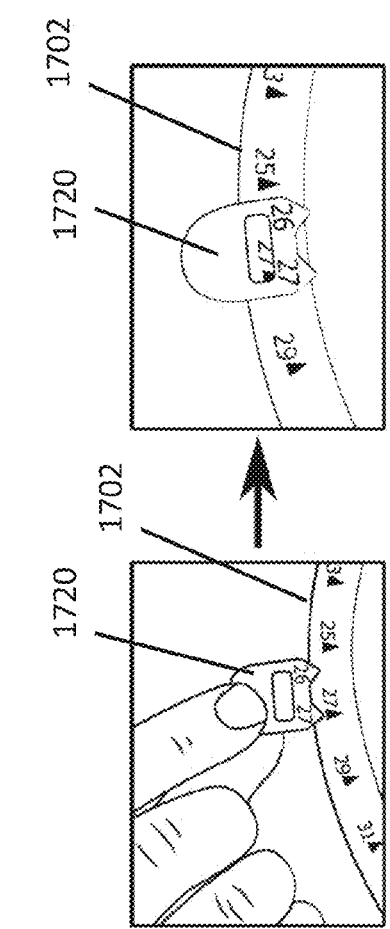
FIG. 17A
FIG. 17C
FIG. 17B

DEVICES AND METHODS FOR AIRWAY MEASUREMENT

CROSS-REFERENCE TO RELATED APPLICATIONS

This application claims priority to U.S. Provisional Application No. 61/900,361 filed on Nov. 5, 2013; U.S. Provisional Application No. 61/938,642 filed on Feb. 11, 2014; U.S. Provisional Application No. 62/006,405 filed on Jun. 2, 2014; and U.S. Provisional Application No. 62/061,109 filed on Oct. 7, 2014, all of which are hereby incorporated by reference in their entirety.

FIELD

The present invention relates generally to devices and methods for mechanically measuring one or more distances in a patient airway.

BACKGROUND

Nasotracheal or orotracheal intubation is commonly used to secure a patient's airway to maintain an open airway, and is frequently used to provide ventilation to the lungs or minimize the possibility of airway obstruction in a patient. In orotracheal intubation, an endotracheal ("ET") tube is inserted through a patient's mouth and into the patient's trachea. In nasotracheal intubation, a nasotracheal tube is inserted through a patient's nostril and into the patient's trachea.

When a patient is intubated, proper placement of the ET tube in the trachea may be important to minimize the possibility of negative complications associated with intubation. For example, if the distal end of the ET tube is not sufficiently advanced into the trachea, there may be an increased risk of accidental extubation when the ET tube is dislodged from the trachea and can no longer maintain an open airway or provide ventilation. Conversely, advancement of the distal end of the ET tube too far into the trachea may cause the ET tube to enter the bronchial passageways. Such bronchial intubation may lead to hypoxia, pneumothorax, or even death. Accordingly, current clinical practice recommends positioning the distal tip of an ET tube between 2 cm and 5 cm proximal to the carina, an anatomical structure located at the bifurcation of the trachea.

Currently, the primary manner of determining positioning of an ET tube is a post-intubation chest x-ray ("CXR"). CXR is generally expensive and exposes the patient to radiation, and is thus not a practical solution for repeated checks. Current alternatives to CXR suffer from several shortcomings. For example, clinical observations such as symmetrical chest expansion and auscultation regularly result in inaccurate tube placement (e.g., incorrect placement in as many as 20% of intubations using clinical observations). Sonography, ultrasound, and bronchoscopy require expensive capital equipment and specialized training, which makes these techniques impractical for frequent usage at many sites of care. Lighted stylets (such as TrachLight™) that use transillumination only provide positioning with respect to external landmarks, which do not necessarily correlate to the location of the carina. Additionally, these lighted stylets may not function properly in certain obese patients, and require a light source which adds expense and a power requirement.

BRIEF SUMMARY

Described here are devices and methods for measuring a distance in the airway of a patient and for positioning or repositioning an ET tube in a patient. In some variations, the device may comprise an inner shaft, where the inner shaft may comprise an expandable stopper positioned at a distal end of the inner shaft. The expandable stopper may be moveable between a low-profile and an expanded configuration. The device may further comprise an outer shaft, which may comprise a lumen through which the inner shaft is slidably disposed, and one or more displacement markings positioned along the inner shaft. In some variations, the inner shaft may comprise a handle at or near a proximal end of the inner shaft. In some variations, the outer shaft may comprise a flared distal end and the expandable stopper may be moveable between a first position in which the expandable stopper is positioned in the flared distal end and maintained in the low-profile configuration and a second position in which the expandable stopper is distally advanced from the flared distal end and in the expanded configuration. In some variations, the expandable stopper may self-expand to the expanded configuration. In some variations the expandable stopper may comprise a plurality of prongs. In some variations, the expandable stopper may comprise an inflatable member. In some variations, the expandable stopper may comprise an expandable foam member.

In some variations, a device for measuring a distance in an airway of a patient intubated with an endotracheal tube may comprise an inner shaft where the inner shaft may comprise a plurality of prongs positioned at a distal end of the inner shaft, where the plurality of prongs is moveable between a low-profile and an expanded configuration. The device may further comprise an outer shaft, which may comprise a lumen where the inner shaft may be slidably disposed. In some variations, one or more displacement markings may be positioned along the inner shaft. In some variations, the inner shaft may comprise a handle at or near a proximal end of the inner shaft. In some variations, the outer shaft may comprise a flared distal end and the plurality of prongs may be moveable between a first position in which the plurality of prongs is positioned in the flared distal end and maintained in the low-profile configuration and a second position in which the plurality of prongs is distally advanced from the flared distal end and in the expanded configuration. In some variations, the plurality of prongs self-expands to the expanded configuration.

A device for measuring a distance in an airway of a patient intubated with an endotracheal tube may comprise an inner shaft, which may comprise an expandable stopper positioned at a distal end of the inner shaft. The expandable stopper may be moveable between a low-profile and an expanded configuration. The device may further comprise an outer shaft, which may comprise a lumen through which the inner shaft is slidably disposed. The device may further comprise one or more alignment markings and a plurality of displacement markings positioned along the device. In some variations, the inner shaft may comprise a handle at or near a proximal end of the inner shaft. In some variations, the plurality of displacement markings may comprise one or more displacement markings associated with each of the one or more alignment markings. In some variations, the one or more alignment markings may be positioned on the outer shaft. In some variations, the plurality of displacement markings may be positioned on the outer shaft. In some variations, the device may comprise an alignment sheath positioned around at least a portion of the outer shaft. In some variations, one or more alignment markings may be positioned on the alignment sheath. In some variations, the plurality of displacement markings may be positioned on the alignment sheath. In some variations, the device may comprise a cap and the outer shaft may be connected to the cap. In some variations of the device that comprise an alignment sheath, the outer shaft and the alignment sheath may be connected to the cap.

A measuring device for measuring a distance in an airway of a patient intubated with an endotracheal tube may comprise an elongate member and an alignment guide. In some variations, the elongate member may comprise an inner shaft, which may comprise an expandable stopper positioned at a distal end of the inner shaft and moveable between a low-profile configuration and an expanded configuration. The elongate member may further comprise an outer shaft comprising a lumen, through which the inner shaft may be slidably disposed, and a plurality of position markings. The alignment guide may comprise a marking indicator and may be configured to attach to a predetermined portion of an endotracheal tube. In some variations, the marking indicator of the alignment guide may be configured to indicate a relative position of the expandable stopper to a distal tip of the endotracheal tube using the plurality of position markings when the elongate member is inserted into the endotracheal tube. In some variations, the alignment guide may comprise indicia to indicate the predetermined portion of the endotracheal tube where the alignment guide may be attached. In some variations, the marking indicator may comprise a viewfinder. The plurality of position markings may comprise a proximal displacement region having a first color, a distal displacement region having a second color, and a medial displacement region having a third color different from the first and second colors. In some variations, the medial displacement region may be configured such that when aligned with the marking indicator, the expandable stopper may be a predetermined distance from a distal tip of the endotracheal tube. In some variations, this predetermined distance may be within 2-5 cm. In some variations, the first and second colors of displacement regions may be the same and in other variations the first and second colors may be different. In some variations, the plurality of position markings may comprise an alignment marking and a plurality of displacement markings. In some of these variations, the alignment marking may be configured to indicate alignment of a distal tip of the endotracheal tube and a distal end of the elongate member when the alignment marking is aligned with the marking indicator. In some variations, the alignment marking may comprise a region having a color. In some variations, the expandable stopper may comprise a plurality of prongs. In some of these variations, the plurality of prongs may comprise at least 5 prongs. In some variations, the plurality of prongs may comprise prongs of different lengths. In some variations, one or more prongs of the plurality of prongs may comprise one or more curves. In some variations, when the plurality of prongs is in the expanded configuration, one or more prongs may comprise a curved proximal portion that may form an angle with a surface parallel to a longitudinal axis of the device that is less than 75 degrees. In some variations, when the plurality of prongs is in the expanded configuration, one or more prongs may comprise an angled distal portion that may form an angle with a surface parallel to a longitudinal axis of the device that is between 1 and 45 degrees. In some variations, the plurality of prongs may comprise atraumatic tips. In some of these variations, the atraumatic tips may comprise ball tips. In some of these variations, each ball tip may have a diameter of 0.065-0.085 inches. In some variations, the outer shaft may comprise a flared distal end that may have a maximum transverse dimension in the range of 4.5-6 millimeters and a middle portion that may have a maximum transverse dimension in the range of 2-4 millimeters.

A method of mechanically measuring a distance in the airway of a patient intubated with an endotracheal tube may comprise advancing an outer shaft of a measuring device through a lumen of the endotracheal tube to align the outer shaft with a predetermined portion of the endotracheal tube. This method may further comprise advancing an inner shaft of the measuring device through a lumen of the outer shaft, beyond a distal end of the outer shaft to at least a distal tip of the endotracheal tube, and further advancing the inner shaft to engage a carina of the patient with the distal end of the inner shaft. This method may further comprise determining a distance between the distal end of the inner shaft and the distal tip of the endotracheal tube while the distal end of the inner shaft engages the carina. In some variations, the inner shaft may comprise an expandable stopper at the distal end of the inner shaft and engaging the carina of the patient with the distal end of the inner shaft may comprise engaging the carina with the expandable stopper. In some variations, the expandable stopper may be moveable between a low-profile configuration and an expanded configuration, and the expandable stopper may be expanded to the expanded configuration after the distal end of the inner shaft has been advanced to at least the distal tip of the endotracheal tube. In some variations, the expandable stopper may self-expand to the expanded configuration. In some variations, the expandable stopper may comprise a plurality of prongs. In some variations, the plurality of prongs may comprise at least 5 prongs. In some variations, the expandable stopper may comprise an inflatable member. In some variations, the expandable stopper may comprise an expandable foam member. In some variations where the outer shaft comprises one or more alignment markings, aligning the outer shaft with the predetermined portion of the endotracheal tube may comprise aligning one or more of the one or more alignment markings with the predetermined portion of the endotracheal tube. In some variations where the endotracheal tube comprises one or more length markings, aligning one or more of the one or more alignment markings with the predetermined portion of the endotracheal tube may comprise aligning one or more of the one or more alignment markings with one or more of the one or more length markings. In some variations, where the inner shaft comprises one or more displacement markings, determining the distance between the distal end of the inner shaft and the distal tip of the endotracheal tube while the distal end of the inner shaft engages the carina may comprise comparing the relative positioning between one or more of the one or more displacement markings and one or more of the one or more alignment markings. In some variations where the inner shaft comprises one or more displacement markings, determining the distance between the distal end of the inner shaft and the distal tip of the endotracheal tube while the distal end of the inner shaft engages the carina may comprise comparing the relative positioning between one or more of the one or more displacement markings and a predetermined portion of the outer shaft. In these variations, the predetermined portion of the outer shaft may be a proximal inlet of the lumen of the outer shaft. In others of these variations, the predetermined portion of the outer shaft may be a window through the outer shaft. In some variations, where the inner shaft comprises one or more displacement markings, determining the distance between the distal end of the inner shaft and the distal tip of the endotracheal tube while the distal end of the inner shaft engages the carina may comprise comparing the relative positioning between one or more of the one or more displacement markings and a predetermined portion of the endotracheal tube. In some of these variations, the predetermined portion of the endotracheal tube may be a proximal tip of the endotracheal tube. In others of these variations, the predetermined portion of the endotracheal tube may be a proximal tip of a connector attached to a proximal end of the endotracheal tube. In others of these variations, the endotracheal tube may comprise one or more length markings that may be the predetermined portion of the endotracheal tube. In some variations, the method may comprise repositioning the endotracheal tube relative to the inner shaft to change the distance between the distal end of the inner shaft and the distal tip of the endotracheal tube. In some variations where the inner shaft comprises a plurality of prongs at the distal end of the inner shaft, engaging the carina of the patient with the distal end of the inner shaft may comprise engaging the carina with one or more of the plurality of prongs. In some variations, where the plurality of prongs is moveable between a low-profile configuration and an expanded configuration, the plurality of prongs may be expanded to the expanded configuration after the distal end of the inner shaft has been advanced at least to the distal tip of the endotracheal tube. In some variations, the plurality of prongs may self-expand to the expanded configuration.

A method of intubating a patient with an endotracheal tube may comprise advancing a distal tip of an endotracheal tube into an airway of the patient to position a distal tip of the endotracheal tube in a trachea and advancing an outer shaft of a measuring device through a lumen of the endotracheal tube to align the outer shaft with a predetermined portion of the endotracheal tube. The method may further comprise advancing an inner shaft of the measuring device through a lumen of the outer shaft to advance a distal end of the inner shaft beyond a distal end of the outer shaft to at least a distal tip of the endotracheal tube. The method may further comprise advancing the inner shaft into the trachea to engage a carina of the patient with the distal end of the inner shaft, and advancing the endotracheal tube and outer shaft relative to the inner shaft while the distal end of the inner shaft engages the carina until the distance between the distal end of the inner shaft and the distal tip of the endotracheal tube is a predetermined distance. In some variations, the predetermined distance may be between 2 cm and 5 cm. In some variations, the inner shaft and outer shaft may be advanced into the lumen of the endotracheal tube prior to advancing the distal tip of the endotracheal tube into the airway of the patient. In other variations, the inner shaft and outer shaft may be advanced into the lumen of the endotracheal tube after advancing the distal tip of the endotracheal tube into the airway of the patient. In some variations, the inner shaft may comprise an expandable stopper at the distal end of the inner shaft and engaging the carina of the patient with the distal end of the inner shaft may comprise engaging the carina with the expandable stopper. In some variations, the expandable stopper may be moveable between a low-profile configuration and an expanded configuration and the expandable stopper may be expanded to the expanded configuration after the distal end of the inner shaft has been advanced distal to the distal tip of the endotracheal tube. In some variations, the expandable stopper may self-expand to the expanded configuration. In some variations, the expandable stopper may comprise a plurality of prongs. In some variations, the expandable stopper may comprise an inflatable member. In some variations, the expandable stopper may comprise an expandable foam member.

A method of intubating a patient with an endotracheal tube may comprise advancing a distal tip of an endotracheal tube into an airway of the patient to position a distal tip of the endotracheal tube in a trachea. This method may further comprise advancing an outer shaft of a measuring device through a lumen of the endotracheal tube to align the outer shaft with a predetermined portion of the endotracheal tube. This method may further comprise advancing an inner shaft of the measuring device through a lumen of the outer shaft to advance a distal end of the inner shaft beyond a distal end of the outer shaft to at least a distal tip of the endotracheal tube. This method may further comprise further advancing a distal end of the inner shaft until the distal end of the inner shaft is a predetermined distance from the distal tip of the endotracheal tube, and advancing the inner shaft, outer shaft, and endotracheal tube together into the trachea until the distal end of the inner shaft to engage a carina of the patient. In some variations, the predetermined distance may be between 2 cm and 5 cm. In some variations, the inner shaft and outer shaft may be advanced into the lumen of the endotracheal tube prior to advancing the distal tip of the endotracheal tube into the airway of the patient. In some variations, the inner shaft and outer shaft may be advanced into the lumen of the endotracheal tube after advancing the distal tip of the endotracheal tube into the airway of the patient. In some variations, the inner shaft may comprise an expandable stopper at the distal end of the inner shaft, and the expandable stopper may engage the carina. In some variations, the expandable stopper may be moveable between a low-profile configuration and an expanded configuration, and the expandable stopper may be expanded to the expanded configuration after the distal end of the inner shaft has been advanced distal to the distal tip of the endotracheal tube. In some variations, the expandable stopper may self-expand. In some variations the expandable stopper may comprise a plurality of prongs. In some variations the expandable stopper may comprise an inflatable member. In some variations, the expandable stopper may comprise an expandable foam member.

A method of mechanically measuring a distance in the airway of a patient intubated with an endotracheal tube may comprise advancing an outer shaft of a measuring device through a lumen of the endotracheal tube to align one or more alignment markings on the measuring device with a predetermined portion of the endotracheal tube. The method may further comprise advancing an inner shaft of the measuring device through a lumen of the outer shaft to advance a distal end of the inner shaft beyond a distal end of the outer shaft. The method may further comprise advancing the outer shaft and the inner shaft to engage a carina of the patient with the distal end of the inner shaft. The method may further comprise determining a distance between the distal end of the inner shaft and the distal tip of the endotracheal tube while the distal end of the inner shaft engages the carina by comparing the relative positioning between one or more of one or more displacement markings on the measuring device and the predetermined portion of the endotracheal tube. In some variations, the endotracheal tube may comprise one or more length markings and aligning the one or more alignment markings with the predetermined portion of the endotracheal tube may comprise aligning the one or more alignment markings with one or more predetermined length markings. In some variations, the one or more alignment markings may be positioned on the outer shaft of the measuring device. In some variations, the one or more displacement markings may be positioned on the outer shaft of the measuring device. In some variations, the measuring device may comprise an alignment sheath positioned around at least a portion of the outer shaft. In some of these variations, one or more alignment markings may be positioned on the alignment sheath. In some of these variations, the one or more displacement markings may be positioned on the alignment sheath. In some variations, the measuring device may comprise a cap and the outer shaft may be connected to the cap. In some variations, the outer shaft and alignment sheath may be connected to the cap.

A method for mechanically measuring a distance in the airway of a patient intubated with an endotracheal tube may comprise coupling an alignment guide to a predetermined portion of the endotracheal tube and advancing an outer shaft of an elongate member through a lumen of the endotracheal tube to align an alignment marking of the elongate member with a marking indicator (e.g., viewfinder) or positioning area of the alignment guide such that the alignment marking is aligned with the marking indicator (e.g. the alignment marking is visible through a viewfinder of the alignment guide). This method may further comprise advancing an inner shaft of the elongate member through a lumen of the outer shaft to advance a distal end of the inner shaft beyond a distal end of the outer shaft. This method may further comprise advancing the outer shaft and inner shaft to engage a carina of the patient with the distal end of the inner shaft, determining a distance between the distal end of the inner shaft and a distal tip of the endotracheal tube while the distal end of the inner shaft engages the carina by identifying the color of at least one of a plurality of displacement markings of the elongate member aligned with the marking indicator (e.g., visible through a viewfinder) of the alignment guide. In some variations, the alignment and displacement markings may be positioned on the outer shaft. In some variations, the elongate member may comprise an alignment sheath positioned around at least a portion of the outer shaft, and the alignment and displacement markings may be positioned on the alignment sheath.

A method of manufacturing a device for measuring a distance in an airway of a patient intubated with an endotracheal tube may comprise shaping each wire of a plurality of wires such that each wire comprises a proximal curved portion and an angled distal portion. This method may further comprise stress-relieving the wires by heating the wires at a temperature of approximately 500-700 degrees Fahrenheit over a period of approximately 5-60 minutes, and the proximal portions of at least two wires may be joined such that the distal ends of the wires form a radially-expandable assembly.

BRIEF DESCRIPTION OF THE DRAWINGS

FIG. 5A depicts a side view of a variation of the distal portion of the measuring devices described here comprising a plurality of prongs with different lengths. An outer shaft of the measuring devices described here has been cut away. FIG. 5B shows an end view of the variation of the distal portion of the measuring device of FIG. 5A.

FIG. 9 depicts an illustrative variation of the measuring devices described here.

FIGS. 11A-11D depict variations of methods by which a measuring device described here may be used during intubation to help position an ET tube relative to the carina of a patient.

FIG. 17A depicts an illustrative variation of the measuring devices described here comprising an elongate member and an alignment guide. FIG. 17B depicts a portion of a method of using an alignment guide of the measuring devices described here. FIG. 17C depicts a variation of an alignment guide of the measuring devices described here.

DETAILED DESCRIPTION

Device and Methods Overview

Figure 1:
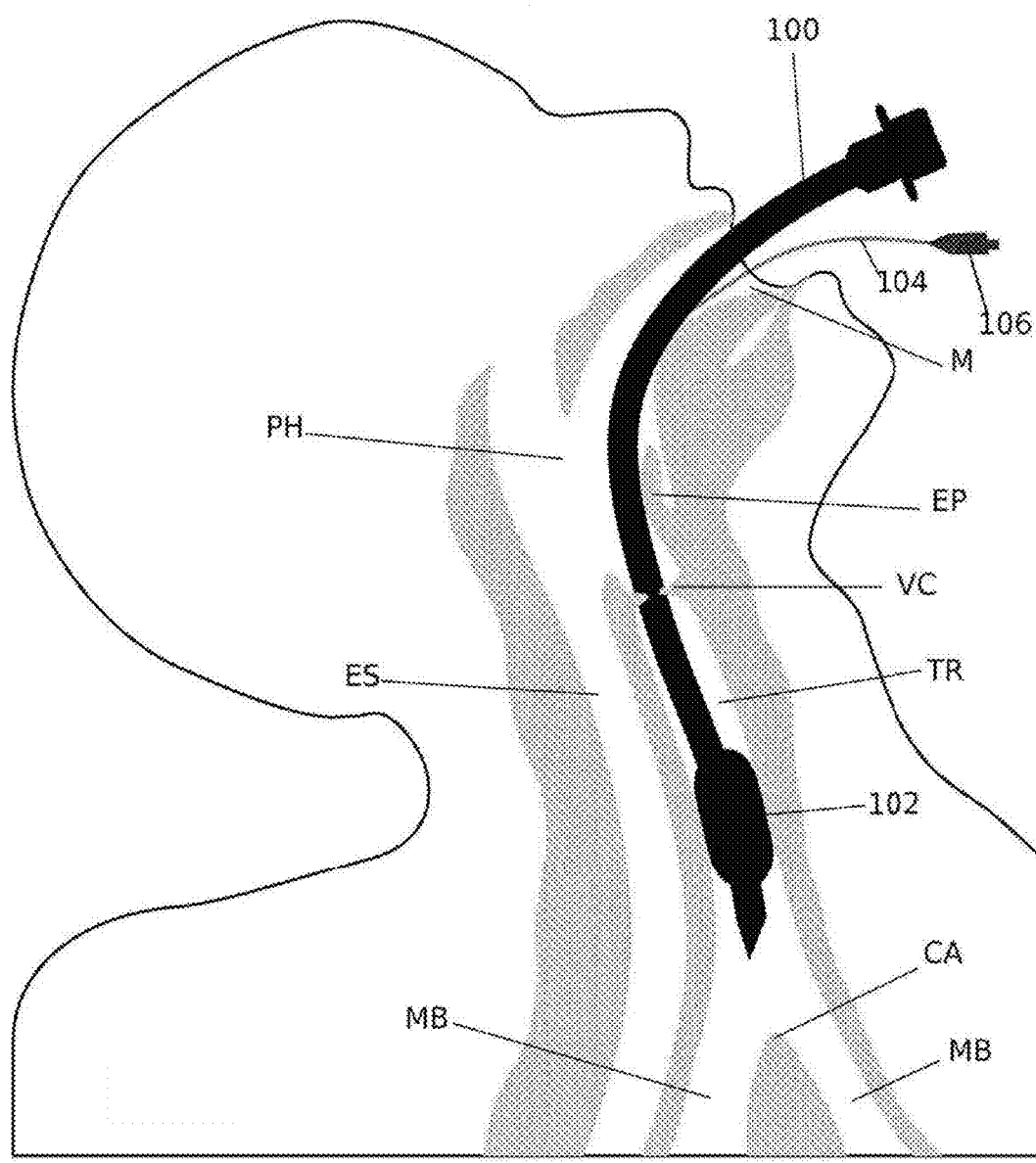
FIG. 1 depicts the anatomy of the upper airway of an intubated patient.

Described here are devices and methods for measuring a distance in the airway of a patient, including distances between a device in the airway and a bifurcation or branch of the airway. In one specific example, the devices and methods described here may be used to measure a separation distance between a distal tip of an endotracheal (ET) tube and the carina. To aid in understanding of the present devices and methods, FIG. 1 depicts portions of the anatomy of the airway of a patient. As shown there, the mouth/oral cavity (M) opens into the pharynx (PH), which divides into the trachea (TR) and the esophagus (ES). The trachea (TR) bifurcates into two main bronchi (MB) (a left main bronchus and a right main bronchus) at the carina (CA). The carina (CA) is a cartilaginous ridge that separates the main bronchi (MB). The main bronchi (MB) feed into the lungs (not shown).

When a patient is intubated with an ET tube, a distal tip of the ET tube is typically advanced through the mouth, past the epiglottis (EP), and into the trachea (TR). For example, the patient shown in FIG. 1 is depicted as having been intubated with an ET tube (100) having an ET balloon (102). When the distal tip of the ET tube (100) has been advanced through the mouth (M) and pharynx (PH) and into the trachea (TR), the ET balloon (102) or occlude may be positioned in the trachea (TR) past the vocal cords (VC). The ET balloon (102) may be inflated (e.g., via an ET inflation port (106) fluidly connected to the ET balloon (102) by an ET inflation tube (104)) in the trachea to form a barrier in the trachea surrounding the ET tube (100). While the ET tube (100) is shown in FIG. 1 as having been introduced through the mouth (M) (e.g., orotracheal intubation), the ET tube (100) may alternatively be a nasotracheal tube introduced through the nose via nasotracheal intubation. It should be appreciated that when devices and methods are described here as being used with an ET tube, the same devices and methods may be used with a nasotracheal tube.

It is typically desirable to position the ET tube within a certain distance (e.g., between 2 cm and 5 cm) from the carina to reduce the risk of accidental extubation or bronchial intubation. Accordingly, the devices and methods described here may be used to measure a distance between an ET tube and carina and/or be used to position the ET tube relative to the carina. The devices described here may allow a user to measure the distance between the distal tip of an ET tube and the carina without the need for x-rays, and may do so in a low-cost and/or disposable manner. Eliminating the need for x-ray confirmation has several benefits. For example, the devices and methods described here may be used to measure the ET tube-carina separation distance frequently without needing to expose the patient to additional radiation. Additionally, nurses and respiratory therapists may be able to check ET tube location without the need for a physician to first order an x-ray. The separation distance may also be measured in locations where an x-ray machine is not readily available (e.g., in emergency medicine vehicles, operating rooms, long term care centers or home care centers).

Examples provided herein may refer to human patients intubated with an ET tube, but it should be appreciated that the variations of devices and methods described herein may be used for humans or animals, live or cadaveric subjects, and may also be used to measure distances of other devices located in non-biologic lumens to a branch or bifurcation of the lumen.

Outer Shaft

Figure 2:
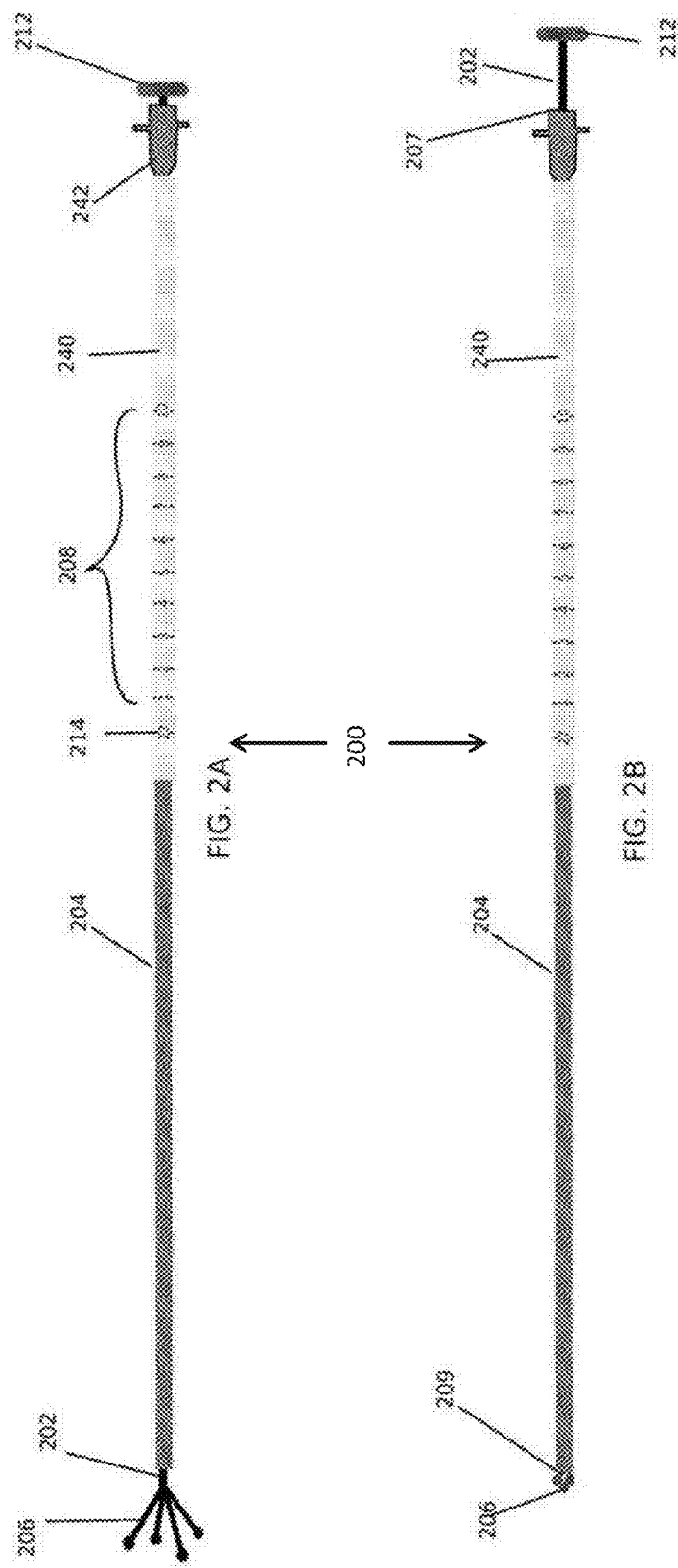
FIGS. 2A and 2B depict an illustrative variation of the measuring devices described here.

FIGS. 2A and 2B show side views of an illustrative variation of the measuring devices described here. As shown in these figures, the measuring device (200) may comprise an inner shaft (202) and an outer shaft (204). The outer shaft (204) may be a tube (e.g., extruded PeBax tubing, polypropylene, polyethylene, or the like) comprising a lumen (not pictured) extending between a proximal inlet (207) and a distal outlet (209). In some variations, the measuring device may further comprise an alignment sheath (240). In some of these variations, the alignment sheath (240) may be a tube which may be positioned around at least a portion of the outer shaft (204). The alignment sheath (240) may be made from the same material or materials as the outer shaft (204), or may be made from different materials as the outer shaft (204). The alignment sheath (240) may in some variations be a different color from the outer shaft (204), which may improve the visualization of alignment markings (214) on the alignment sheath relative to length markings of the ET tube, as will be discussed in more detail below. In some instances, the alignment sheath (240) may be bonded to the outer shaft (204) to fix the alignment sheath (240) thereto. It should be appreciated, however, that in some variations, the measuring device (200) does not comprise an alignment sheath (240), and any markings that would be positioned on the alignment sheath (240), as discussed below, may be located directly on the outer shaft (204).

The outer shaft (204) may comprise a cap (242) on the proximal end. This cap (242) may provide a gripping mechanism, which may allow a user to manipulate the outer shaft (204). In some variations where the measuring device (200) comprises both an outer shaft (204) and an alignment sheath (240), the outer shaft (204) and the alignment sheath (240) may each be connected to the cap (242), which may help provide strain relief between the outer shaft (204) and the cap (242).

Inner Shaft

In some variations, the inner shaft (202) may be a tube (e.g., an extruded Pebax shaft, which in some instances may be extruded over a metal rod, polypropylene, polyethylene) with a lumen (not shown) extending therethough. In these variations, the lumen of the inner shaft (202) may allow for aspiration through the inner shaft (202). It should be appreciated that a suction source may alternatively be connected to an outlet along a length of the inner shaft (202). In some variations, the inner shaft (202) may not comprise a lumen. In some variations, the inner shaft (202) may comprise a handle (212). The handle (212) may be positioned at or near the proximal end of the inner shaft (202), and may provide a gripping mechanism that may facilitate manipulation of the inner shaft (202) by a user. In some variations, the handle (212) may be sized or otherwise configured such that it is prevented from entering the outer shaft (204) (e.g., via the proximal inlet (207) of the outer shaft (204)). In other variations, the handle (212) may be configured such that it releasably engages with the cap (242) attached to the outer shaft (204) through a threaded connection, a press-fit connection, or the like.

The inner shaft (202) may be sized to fit at least partially within the lumen (not pictured) of the outer shaft (204). The inner shaft (202) may be advanced relative to the outer shaft (204) to move a distal end of the inner shaft (202) out of the distal outlet (209) of the outer shaft. The inner shaft (202) may be retracted relative to the outer shaft (244) to pull the distal end of the inner shaft (202) into the lumen (205) through the distal outlet (209) of the outer shaft.

In some variations, the use of an inner and outer shaft may be advantageous. For example, as is described in more detail herein, an outer shaft may constrain an expandable stopper on a distal end of an inner shaft in a low-profile configuration while the expandable stopper is within a lumen of the outer shaft. This may allow a user to maintain the expandable stopper in the low-profile configuration (e.g., for introduction of the measuring device into an ET tube or withdrawing the measuring device from an ET tube) by manipulating proximal ends of the inner and outer shafts. This configuration may reduce the need to handle the expandable stopper directly, which may reduce the risk of contaminating the expandable stopper with infectious material that may then enter a patient's airway. An advantage of this configuration may be that the expandable stopper does not contact inner walls of the ET tube lumen while the measuring device is being moved relative to the ET tube. This may reduce the risk of unintentionally dislodging the ET tube.

Expandable Stopper

Figure 3:
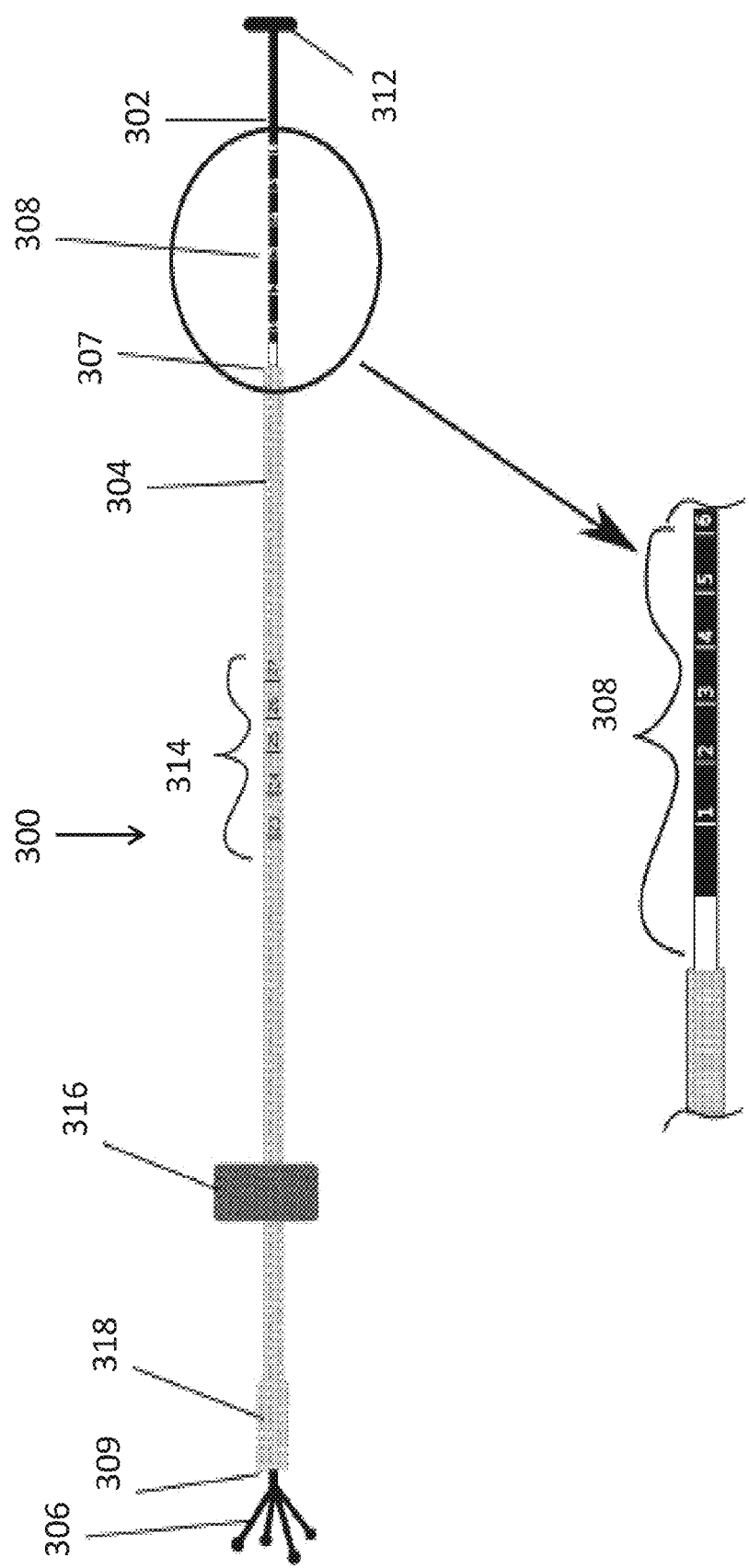
FIG. 3 depicts an illustrative variation of the measuring devices described here.

As shown in FIG. 3, the inner shaft (302) of a measuring device (300) may comprise an expandable stopper (306) or catching structure at a distal end of the inner shaft (302). The expandable stopper (306) or catching structure may be moved from a low-profile configuration to an expanded configuration, and may be configured to catch on or otherwise engage airway tissue such as the carina when advanced through the trachea in an expanded configuration, as will be described in more detail below. In some variations, the outer shaft (304) may optionally comprise a flared end (318) to receive and accommodate the expandable stopper (306) or catching structure when in the low-profile configuration.

The expandable stopper may be any suitable expandable structure capable of catching or otherwise being stopped by the bifurcation or branching of the trachea at the carina. For example, in some variations the expandable stopper may comprise an expandable foam structure. In these variations, the foam structure may be expanded in the trachea to a size larger than the main bronchi, such that the foam structure may catch on the carina as the foam structure reaches the bifurcation of the trachea. The foam structure may be constrained to a low-profile configuration (e.g., by pulling the foam structure into the lumen of an outer shaft). The foam structure may have any suitable shape (e.g., a spherical shape, a cylindrical shape, or the like).

In other variations, the expandable stopper may comprise an expandable loop. In yet other variations, the expandable stopper may comprise an inflatable structure such as a balloon. In these variations, the inflatable structure may be inflated in the trachea to move the inflatable structure from a low-profile configuration to an expanded configuration. When inflated in the trachea, the inflatable structure may have a size larger than the main bronchi, such that the inflatable structure may catch on the carina as the inflatable structure reaches the bifurcation of the trachea. The inflatable structure may have any suitable shape (e.g., a spherical shape, a cylindrical shape, or the like).

Figure 4A:
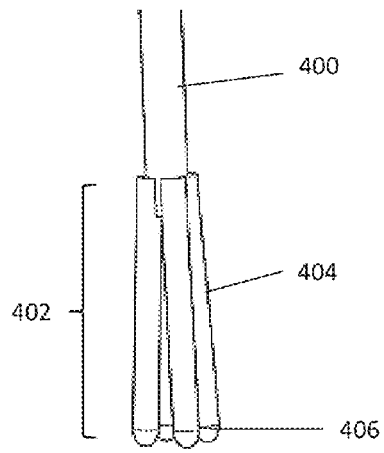
FIGS. 4A-4D depict variations of distal portions of the measuring devices described here comprising a plurality of prongs.
Figure 4B:
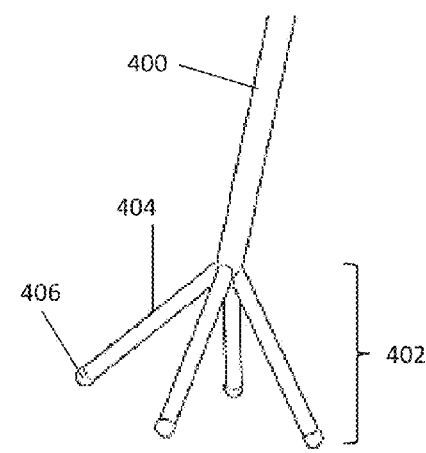

In still other variations, the expandable stopper comprises a pronged structure having a plurality of prongs. The pronged structure may comprise any suitable number of prongs. In some variations, the pronged structure may comprise at least two, three, four, five, six or seven prongs. FIGS. 4A and 4B show a variation of a distal end of a shaft (400) comprising an expandable stopper (402) comprising a plurality of prongs (404). As shown there, the expandable stopper (402) comprises four prongs (404), although it should be appreciated that the expandable stopper (402) may comprise any suitable number of prongs as described above.

When an expandable stopper comprises a plurality of prongs, the prongs may engage the carina by catching the bifurcation of the trachea at the carina between at least two of the prongs. In some variations, an expandable stopper with five or more prongs may be advantageous to increase the likelihood that at least two prongs will be located on the side of the trachea bifurcation towards the left main bronchus and at least two prongs will be located on the side towards the right main bronchus. This may reduce the risk that the resistance to advancing the stopper past the bifurcation may be inadvertently overcome.

When an expandable stopper comprises a plurality of prongs, the prongs may be moveable relative to the shaft to move the expandable stopper between low-profile and expanded configurations. For example, FIG. 4A shows the expandable stopper (402) in a low-profile configuration and FIG. 4B shows the expandable stopper (402) in an expanded configuration. To move the expandable stopper (402) from the low-profile configuration to the expanded configuration, the prongs (404) may rotate, bend, or otherwise deflect away from the longitudinal axis of the shaft (400) to increase the distance between the prongs (404). Conversely, the prongs (404) may rotate, bend, or otherwise deflect toward the longitudinal axis of the shaft (400) and each other to return the prongs (404) to the low-profile configuration. When the plurality of prongs (404) is in an expanded configuration, the distal ends of the prongs (406) may define an outer profile having any suitable diameter. For example, in some variations, the outer profile diameter may be greater than 25 mm. In some of these variations, it may be advantageous to have a diameter between 25 mm and 35 mm.

An expandable stopper comprising a plurality of prongs may be moved from a low-profile to an expanded configuration in any suitable manner. In some variations, the prongs may be deformed or otherwise manually expanded from the low-profile configuration to the expanded configuration (e.g., by inflating a balloon between the prongs). In other variations, the prongs may self-expand from the low-profile configuration to the expanded configuration. In these variations, the prongs may be formed or otherwise connected to the shaft such that they are biased toward the expanded configuration. To move the prongs to the low-profile configuration, a constraining force may be applied to the prongs to overcome the bias towards the expanded configuration. For example, the plurality of prongs may be withdrawn into a lumen of an outer shaft, and the lumen of the outer shaft may constrain the plurality of prongs to a low-profile configuration. When the plurality of prongs are advanced from the outer shaft (thereby removing the constraining force on the prongs), the plurality of prongs may self-expand to the expanded configuration. In other instances, the expandable stopper may be compressed (e.g., manually) and may be inserted into the ET tube, such that the ET tube may constrain the plurality of prongs. When the plurality of prongs are advanced from the ET tube (thereby removing the constraining force on the prongs), the plurality of prongs may self-expand to the expanded configuration.

Figure 4C:
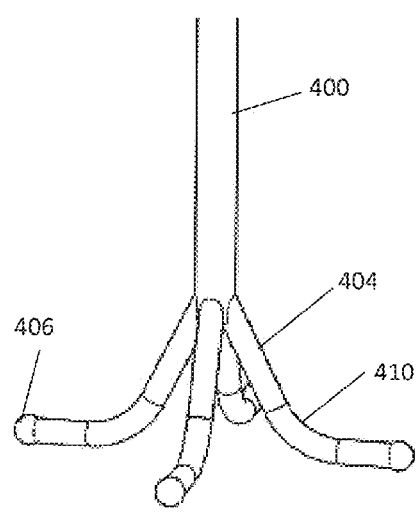

When the plurality of prongs are in an expanded configuration, some or all of the prongs may be straight or some or all of the prongs may comprise one or more curves or bends. For example, in the variation of the plurality of prongs (404) shown in FIG. 4B, each of the prongs (404) may be straight when the plurality of prongs are in the expanded configuration. FIG. 4C shows another variation of a shaft (400) comprising a plurality of prongs (404). As shown there, each prong (404) may comprise a curved portion (410) along the length of the prong (404). In these variations, the prongs (404) may begin expanding prior to the entire prong (404) being released from a constraining force provided by an outer sheath or ET tube, and may take on a larger outer profile when expanded. In still other variations, the plurality of prongs may be configured such that at least one prong is straight and at least one prong has a curved or bent portion when the plurality of prongs is in an expanded configuration.

Figure 4D:
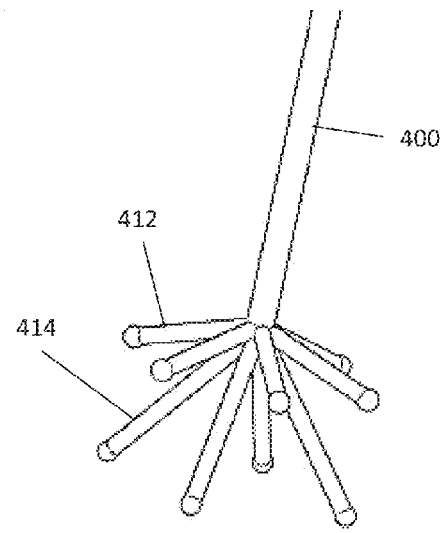

In some variations, each prong of the plurality of prongs may be the same length. In other variations, an expandable stopper may comprise a plurality of prongs having different lengths. For example, FIG. 4D shows a variation of a shaft (400) that comprises a first plurality of prongs (412) each having a first length and a second plurality of prongs (414) each having a second length longer than the first length. In some embodiments, configurations of the expandable stopper comprising prongs of different lengths may be advantageous in that the low-profile configuration may be more compressed than configurations comprising prongs of the same length. As will be discussed in more detail below, each prong may comprise an atraumatic coating or structure at its distal end, which may reduce the risk of piercing or snagging tissue as the device is advanced along a body passage. In one example, the atraumatic structure may be a rounded and/or bulbous distal ball tip, which may limit the compressibility of the plurality of prongs in a low-profile configuration.

FIGS. 5A (side view) and 5B (top view) show a variation of an expandable stopper (502) with a plurality of prongs (504) with different lengths and ball tips (506), constrained within the lumen (508) of an outer shaft (510) in a low-profile configuration. As is seen there, the different lengths of prongs (504) may result in the ball tips (506) being staggered when the expandable stopper (502) is in the low-profile configuration. The profile diameter (512) of the prongs and ball tips may be less than the profile diameter in configurations where the ball tips are not staggered. In variations of the measuring device comprising a self-expanding expandable stopper that may be withdrawn into an outer shaft lumen, a more compressed low-profile configuration (e.g., smaller profile diameter) of the expandable stopper may allow for the outer shaft to have a smaller diameter. For example, in some variations, a portion of the outer shaft that may be inserted into an ET tube may comprise a flared distal portion to accommodate an expandable stopper in the low-profile configuration and a narrower middle portion. In some of these variations, the flared distal portion may have a maximum transverse dimension in the range of about 4.5 mm to about 6 mm. The middle portion may have a maximum transverse dimension in the range of about 2 mm to about 4 mm. A transverse dimension may be defined as a dimension that is in a plane that is perpendicular to a longitudinal axis of the outer shaft (i.e. the axis through the proximal inlet and the distal outlet of the outer shaft). A smaller outer shaft diameter may produce less airway resistance when it is within a patient's airway, which may by clinically advantageous. It should also be appreciated that in variations where an expandable stopper comprises a plurality of prongs, each prong may have any suitable angle with respect to the inner shaft when the plurality of prongs is in an expanded configuration. In some variations, each prong may have the same angle relative to the inner shaft. In other variations, different prongs may have different angles with respect to the shaft.

In some variations, the plurality of prongs may be configured to promote atraumatic contact with tissue during advancement of the expandable stopper. For example, in the variation of the expandable stopper (502) shown in FIGS. 5A and 5B, the prongs (504) may comprise a rounded and/or bulbous ball tip (506). The ball tips (506) may be integrally formed with the prongs (504), or may be formed separately (e.g., by overmolding or dipping the prongs (504) or by any suitable molding process (e.g., injection, blow, rotational)). In some variations, the ball tips (506) may be formed by dipping the prongs (504) in an acrylic adhesive. In some variations, the prongs (504) may be dipped 1-3 times into adhesive with the same or different viscosities (e.g., 600-1600 cP). The dipping rate may be the same or different each time the prongs are dipped. In some variations, the ball tips (506) may be an inflatable structure or a soft foam or sponge structure configured to provide a softer tissue contact surface. A soft structure of the ball tips may also allow for the prongs to be more compressed in a low-profile configuration. In some variations, the ball tips may have a diameter of 0.065-0.085 inches, which may be advantageous for reducing the risk of damaging airway tissue and/or for compressing to a desirable profile diameter (512) when the stopper is the low-profile configuration.

Figure 6:
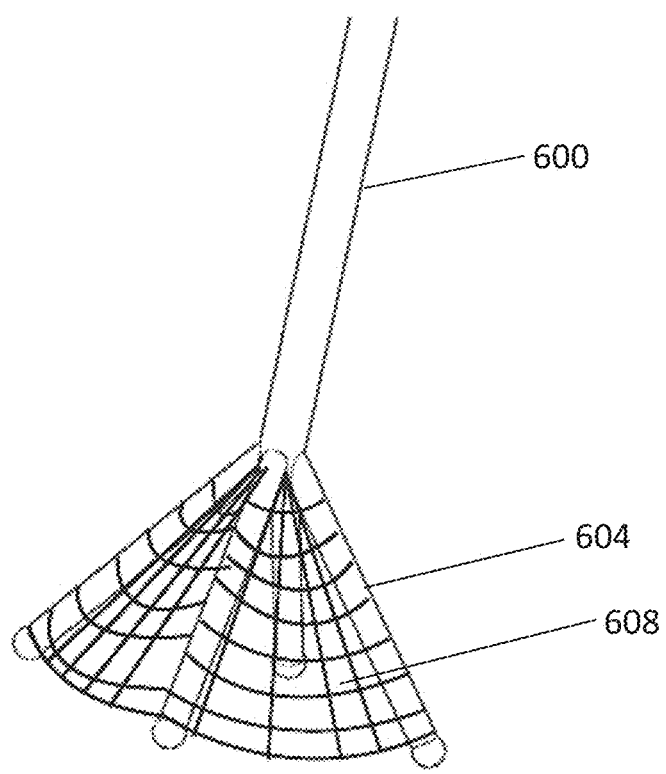
FIG. 6 depicts a variation of the distal portion of the measuring devices described here comprising a plurality of prongs and webbing.

Additionally or alternatively, the plurality of prongs may comprise a webbing, mesh, or foam connecting adjacent prongs, which provide a softer contact surface to the carina when caught between two prongs. For example, FIG. 6 shows a variation of shaft (600) comprising a plurality of prongs (604) and webbing (608) connecting adjacent prongs (604). It should be appreciated that the expandable stoppers may comprise a plurality of prongs including any combination of the features described herein.

Figure 7A:
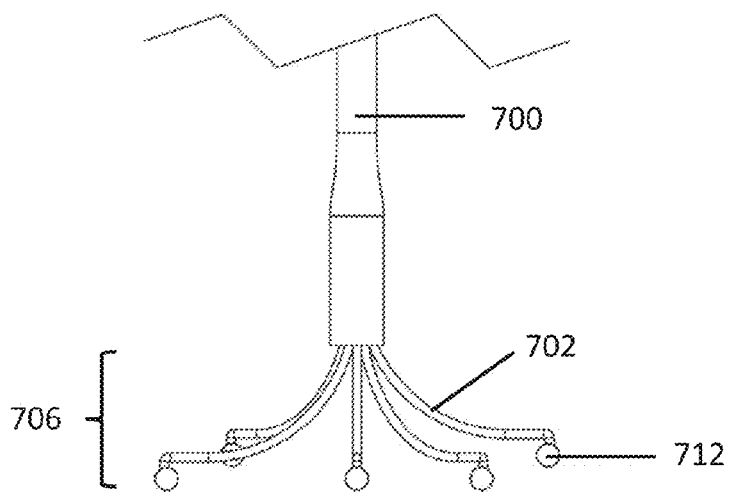
FIG. 7A depicts a variation of the distal portion of the measuring devices described here comprising a plurality of prongs and ball tips in an expanded configuration.
Figure 7B:
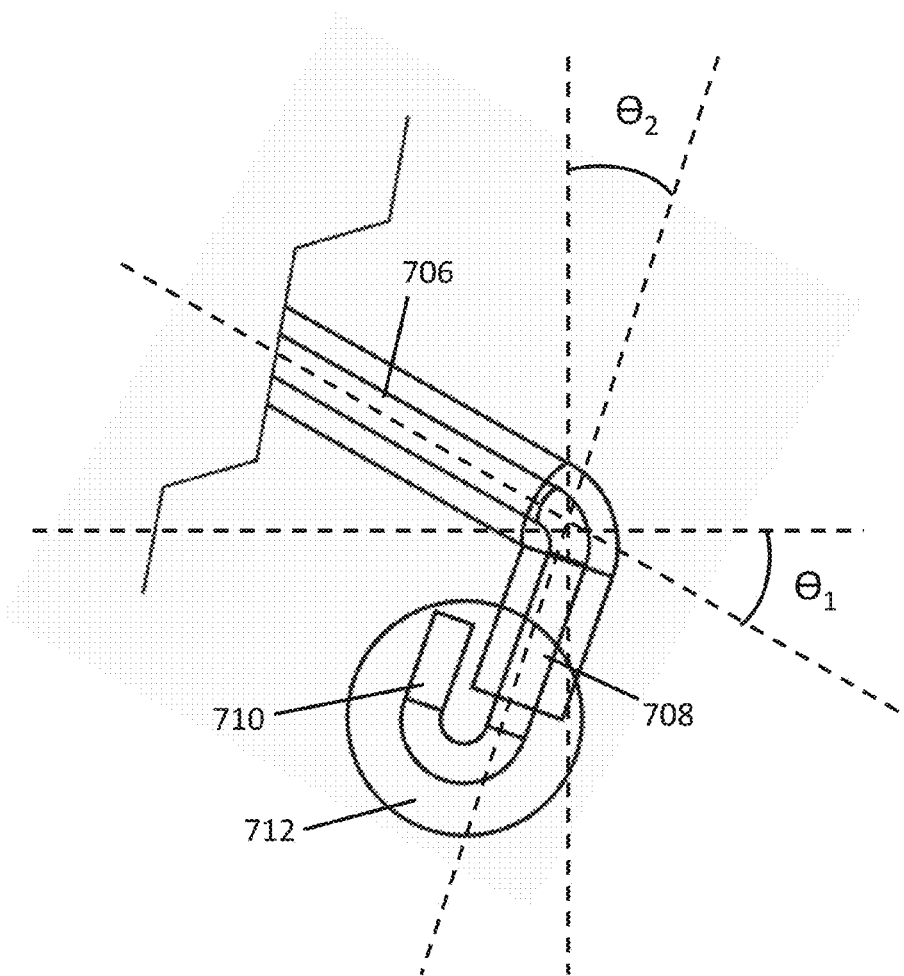
FIG. 7B is a schematic of the distal portion of one prong of the measuring device of FIG. 7A.

In some variations of the measuring device, as shown in FIG. 7A, the prongs (702) of the expandable stopper (706) may be shaped to facilitate deployment of the measuring device (e.g., to reduce the risk of trauma to tissue during advancement in a body lumen, or otherwise shaped for a particular anatomy or purpose). In one exemplary embodiment, the expandable stopper (706) comprises five prongs (702), but may comprise fewer or more prongs (702) as desired. As shown in FIGS. 7A and 7B, the prongs (702) may comprise a curved proximal portion (706), with $\theta_1$ being greater than zero (e.g., at least approximately 15 degrees) where the curved proximal portion contacts a surface (e.g., the trachea wall) that is parallel to the longitudinal axis of a measuring device shaft (700). Additionally, the prongs (702) may comprise an angled distal portion (708), which may facilitate deflection of the prongs (702) distally in an airway, with $\theta_2$ being greater than zero but less than approximately 45 degrees. In some variations, the prongs may comprise a distal kink (710), which may help to retain a ball tip (712) in some manufacturing processes, such as when the prongs are dipped in a material (e.g., acrylic adhesive) to form the ball tip. However, the prongs (702) may be curved and/or angled along different portions of the expandable support mechanism (706) in any suitable manner.

One exemplary method of manufacture involves shaping each prong individually, such as with a spring forming machine. Each prong may comprise a round stainless steel wire with a diameter of approximately 0.007-0.019 inches, or a flat stainless steel wire with a thickness of 0.005-0.018 inches and a width of 0.005-0.018 inches but at least one prong may comprise any suitable material. In some variations, the use of a round stainless steel wire with a diameter 0.011-0.013 inches may be advantageous. A stainless steel wire of this diameter may deflect at forces (e.g., less than 0.2 lbf) that are low enough to reduce the risk of airway tissue trauma, provide adequate tactile feel to a user when the prongs engage the carina, and/or minimize the risk of creep of the formed wire over time. The prong may be formed out of different stainless steel alloys including 302, 304, 302/304, 316, 17-7 or 17-4. The shaped wire may be stress relieved by heating the wires at a temperature of 500-700 degrees Fahrenheit (and more particularly, at approximately 600 degrees Fahrenheit) for a period of 5-60 minutes (and more particularly, for approximately 30 minutes). This stress relief may help maximize material elasticity and minimize creep over time. In other methods of manufacture, at least a portion of the prongs of the expandable stopper may be formed through injection molding, nitinol forming, stainless steel forming, and/or any suitable process.

After shaping and/or stress relieving the wires, the proximal portions of two or more wires may be joined together to form a distal plurality of prongs in an expanded form. The wires may be joined, for example, by bonding, crimping or twisting. However, the wires may be joined in any suitable manner and in any combination of methods. Additionally, the wires may be covered with a plastic sheath (e.g., Pebax or another polymer) and/or one or more other coatings.

Sealing Member

Figure 8A:
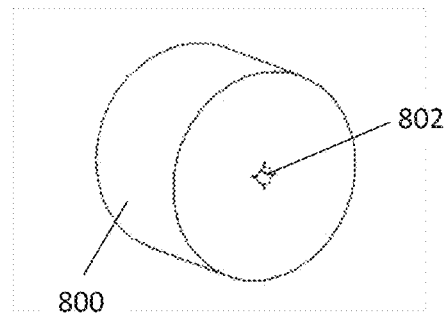
FIGS. 8A-8D depict variations of sealing members suitable for use with the measuring devices described here.
Figure 8B:
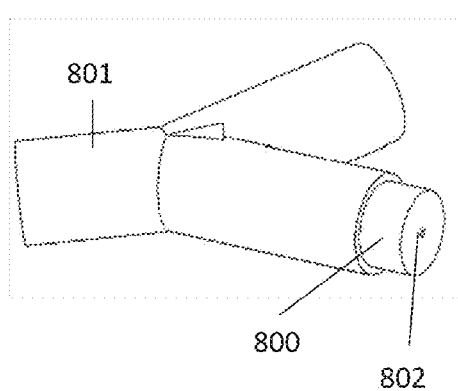

In some variations, the measuring devices described here may optionally comprise a sealing member configured to block airflow through an opening of an ET tube or a connector attached thereto. For example, in some variations, the sealing member may comprise a plug configured to fit at least partially inside the ET tube or connector opening. In these variations, the plug may fill the opening to prevent airflow therethrough. The plug may comprise a channel or lumen extending therethrough to allow an inner shaft and/or outer shaft of the measuring device to pass through the plug. The plug may be formed from any suitable material, such as a sponge, foam, or rubber material. When a shaft of a measuring device is passed through a channel or a lumen, the shaft may compress the material of the plug, which may cause the plug to seal against the shaft. For example, FIG. 8A shows a variation of a plug (800) comprising a lumen (802) extending therethrough. The plug (800) may be inserted into an opening of an ET tube or connector to seal the opening. For example, FIG. 8B shows the plug (800) positioned in an opening of a wye connector (801), which may seal the opening of the wye connector. One or more portions of the measuring device may be positioned through the lumen (802) to allow the measuring device to be manipulated through the sealed opening in the wye connector (801).

Figure 8C:
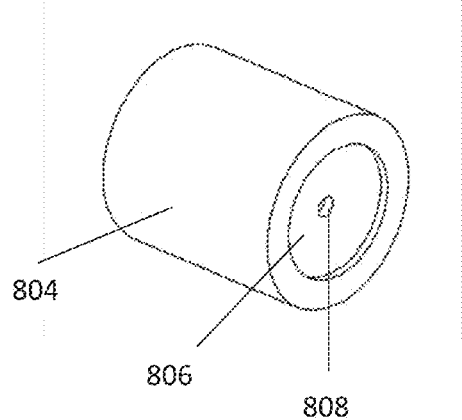
Figure 8D:
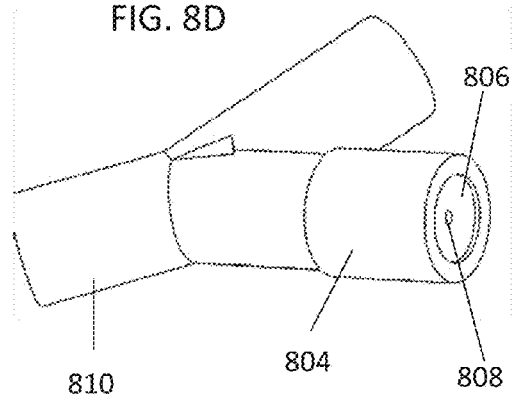

In other variations, the sealing member may comprise a cap configured to fit at least partially around an exterior portion of the ET tube and to cover the opening of the ET tube or connector. The cap may comprise a channel or lumen extending therethrough to allow an inner shaft and/or outer shaft of the measuring device to pass through the cap. The cap may be formed from any suitable material, such as, for example, a sponge, foam, or rubber material. In some variations, the cap may be formed from multiple components. For example, FIG. 8C shows a variation of a cap which may comprise a connector (804), a membrane (806), and a membrane lumen (808). The connector (804) may be configured to sealingly fit around an ET tube or connector, and may be rigid, flexible or the like. For example, FIG. 8D shows the cap positioned around an opening of a wye connector (810) to seal the opening of the wye connector. The membrane (806) may comprise a lumen (808) through which a shaft or other component of the measuring device may be introduced. The membrane (806) may be made from a flexible or compressible material (such as a sponge, foam, or rubber material), which may be compressible to allow a shaft of the measuring device to pass through the membrane (806) while creating a seal around the shaft. Alternatively, a cap may comprise a connector and a sealing valve, such as a Tuohy Borst valve or the like.

Securement Mechanism

The measuring devices described here may optionally comprise a securement mechanism configured to temporarily fix an outer shaft of the measuring device relative to the ET tube. In some variations, the securement mechanism may comprise a cap or plug as described in more detail herein. In variations where the securement mechanism comprises a plug, insertion of the plug into the opening of the ET tube or a connector may create a temporary friction fit between the plug and the ET tube. Similarly, the plug may be configured to have a friction fit with the outer shaft, such that the plug resists movement of the outer shaft. Accordingly, when the plug is inserted into the ET tube or connector, the plug may hold the outer shaft in place relative to the ET tube. In order to move the outer shaft relative to the ET tube, a user may apply a strong enough pushing or pulling force to the outer shaft to temporarily overcome the frictional force between the plug and the outer shaft. In variations where the securement mechanism comprises a cap, the cap may also be configured to form a friction fit with the ET tube or connector and the outer shaft. In other variations, the securement mechanism may comprise one or more clips or clamps configured to temporarily connect the outer shaft to the ET tube or a connector attached thereto.

Variations of Alignment and Displacement Markings and Methods for Use of the Device with Each Variation A measuring device as described here may comprise a plurality of position markings that may allow for measurement of an airway and positioning of an ET tube. In some variations, these position markings may comprise one or more alignment and/or displacement markings. Generally, alignment markings may be used to align the device with a position on an ET tube that is a known distance from the distal tip of the ET tube. Commercially available ET tubes are commonly labeled with length markings along the length of the tube to indicate the distance between each length marking and the distal tip of the ET tube. Generally, these length markings may be spaced at either even distance intervals (e.g., a tube may comprise length markings at 24 cm, 26 cm, and 28 cm from the distal tip of the ET tube) or odd distance intervals (e.g., a tube may comprise length markings at 23 cm, 25 cm, and 27 cm from the distal tip of the ET tube). Alignment markings on the measuring device may be located a known distance from the distal end of the measuring device. Accordingly, alignment of an alignment marking on the measuring device with a length marking on the ET tube may allow a user to determine the distance between the distal end of the measuring device and the distal tip of the ET tube. For example, alignment of an alignment marking on a measuring device that is 26 cm from the distal end of the measuring device with a 26 cm length marking on an ET tube will align the distal end of the device with the distal tip of the ET tube. The expandable stopper may then be aligned with the distal end of the device and the distal tip of the ET tube.

One or more displacement markings may indicate the distance the expandable stopper has moved from its position when initially aligned. In variations of the measuring device and methods where alignment of the measuring device with an ET tube also aligns the expandable stopper with the distal tip of the ET tube, displacement markings may indicate the distance between the stopper and the distal tip of the ET tube. In these methods, when the expandable stopper engages the carina, the displacement markings may indicate the distance between the carina and the distal tip of the ET tube.

Positioning of markings that may be used to measure a distance between an expandable stopper and another element (e.g., the distal end of the outer shaft, distal tip of the ET tube) may take into account the design of the expandable stopper and/or the way in which it engages the carina. For example, in variations of the stopper comprising a plurality of prongs, the stopper may engage the carina in such a way that the vertex of the plurality of prongs is at the level of the carina. Markings (e.g., displacement markings) may be configured to indicate distances from the vertex of the plurality of prongs in these cases. In other variations of an expandable stopper, such as those that comprise a solid element with a diameter greater than the diameter of a main bronchus (e.g., expandable foam), a distal portion of the stopper may engage the carina. Accordingly, markings (e.g., displacement markings) may be configured to indicate distances between the distal portion of the stopper and another element (e.g., the distal end of the outer shaft, distal tip of the ET tube).

Multiple variations for how position markings may be configured on the measuring device will be described. For example, in some variations of the device, position markings comprise displacement markings on an inner shaft, whereas in other variations position markings comprise displacement markings on an outer shaft. The methods for using the device may be different for different configurations of position markings, and these different methods will be described as well.

Variation of Device with Numerical Displacement Markings on Inner Shaft

As shown in FIG. 3, the inner shaft (302) may comprise one or more displacement markings (308), which may be positioned along a proximal portion of the inner shaft (302). The displacement markings (308) may be used to measure the relative positioning between the expandable stopper (306) and a distal end of the outer shaft (304) and/or a portion of an ET tube (e.g., the distal tip of the ET tube).

Further as shown in FIG. 3, the outer shaft (304) may comprise one or more alignment markings (314). In variations of the device that comprise an alignment sheath, one or more alignment markings may be positioned on the alignment sheath. The one or more alignment markings (314) may be aligned with one or more portions of an ET tube to set an initial relationship between the positioning of the outer shaft (304) and the ET tube. For example, in some variations, the distal end of the outer shaft (304) may be aligned with a distal tip of the ET tube when an alignment marking (314) is aligned with a corresponding distance marker on the ET tube.

The relative positioning between the displacement markings (308) of the inner shaft (302) and the one or more alignment markings (314) or another portion of the outer shaft (304) may indicate the relative positioning between the expandable stopper (306) and the outer shaft (304), which in turn may indicate the relative positioning between the expandable stopper (306) and the ET tube. The relative positioning between the expandable stopper (306) and the ET tube may be used to measure the distance between the distal tip of the ET tube and a portion of the patient airway, as will be discussed in more detail below.

While the measuring device shown in FIG. 3 comprises both an inner shaft (302) and an outer shaft (304), it should be appreciated that in some variations, the measuring devices described here may not comprise an outer shaft (304). For example, FIG. 9 shows a variation of a measuring device (900) comprising a elongate shaft (902), an expandable stopper (904) positioned at a distal end of the elongate shaft (902), and one or more markings (906) positioned along the length of the elongate shaft (902). In these variations, the expandable stopper (904) may be configured to expand within the trachea and may be configured to engage the carina, as was described in more detail above. The one or more markings (906) may be used to align the elongate shaft (902) with an ET tube and to measure the distance between a distal tip of the ET tube and the carina, as will be described in more detail below.

Measurement Methods

As mentioned above, the measuring devices described here may be used to measure a distance in the airway. For example, in some variations, the measuring device may be used to measure a distance between an ET tube (e.g., a distal tip of the ET tube) and the carina. This may allow a user or practitioner to determine the positioning of the ET tube in a patient's airway, and to reposition the ET tube if necessary. In some instances, the measuring device may be used to aid in placement of the ET tube at a desired location in the airway (e.g., 2 cm to 5 cm from the carina).

Figure 10A:
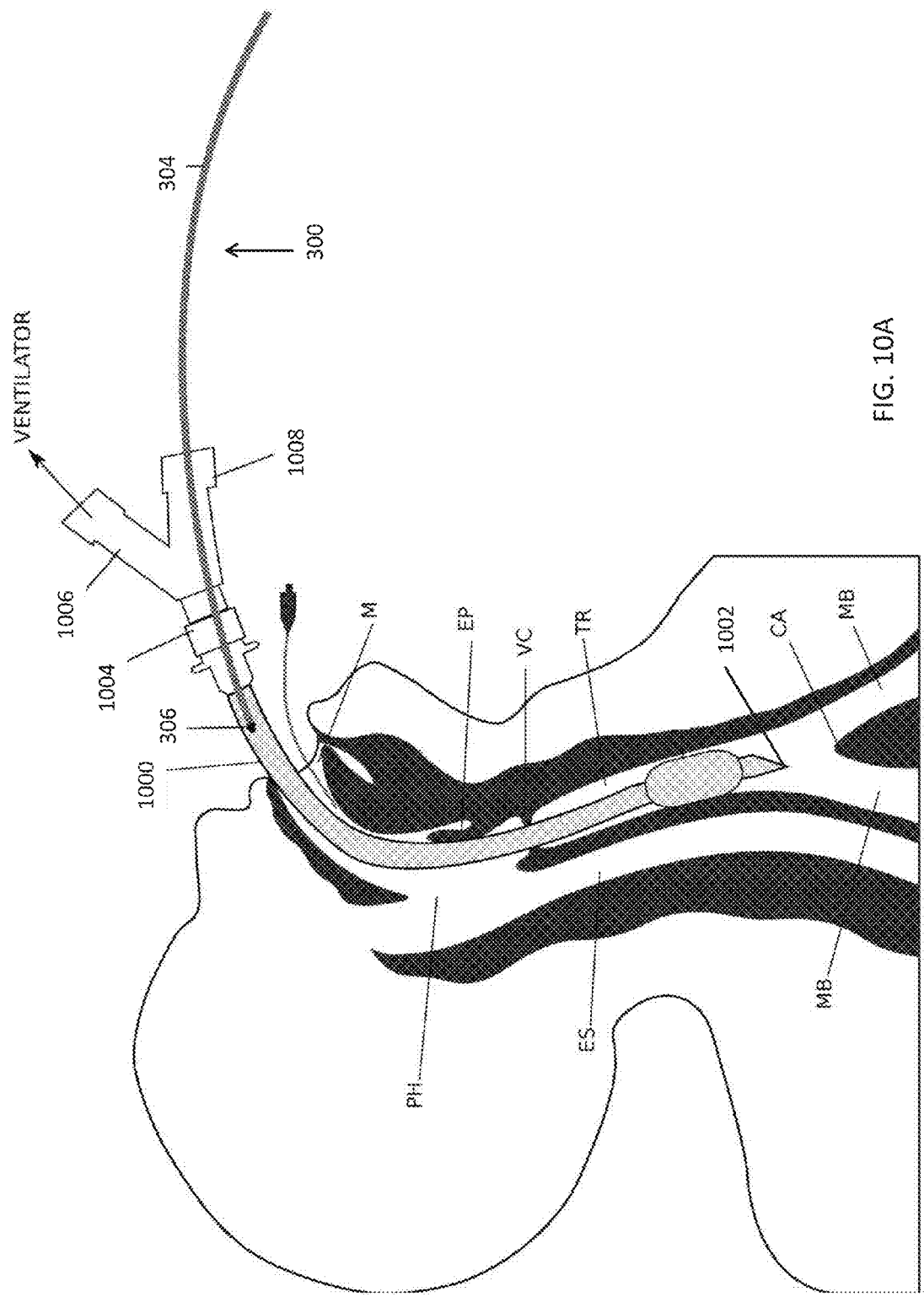
FIGS. 10A-10H depict variations of methods by which a measuring device described here may be used to measure a distance between a distal tip of an ET tube and the carina of an intubated patient.

FIGS. 10A-10H depict a method by which the measuring devices comprising displacement markings on an inner shaft may be used to determine placement of an ET tube relative to the carina. As shown in FIG. 10A, a patient may be intubated with an ET tube (1000) to position a distal tip (1002) of the ET tube in the trachea (TR) (the anatomical structures are labeled the same as in FIG. 1). For the purposes of illustration, the measuring device (300) described above with respect to FIG. 3 is shown in FIGS. 10A-10H to measure a distance between the ET tube (1000) and the carina (CA), but it should be appreciated that any variations of the measuring device with displacement markings on the inner shaft may be used in the methods described here.

Introduction of Device into ET Tube

With the patient intubated, a distal end of the measuring device (300) may be inserted into a proximal end of the ET tube (1000), as shown in FIG. 10A. In some variations, the measuring device (300) may be inserted directly into the proximal end of the ET tube (1000). In other variations, one or more connectors may be attached to the proximal end of the ET tube (1000), and the measuring device (300) may be advanced into the proximal end of the ET tube (1000) through the connector (e.g., the measuring device (300) may be introduced into an inlet of the connector and advanced through the connector to the ET tube (1000)). For example, as shown in FIG. 10A, a connector (1004) may be attached to a proximal end of the ET tube (1000). The connector (1004) may comprise a first branch (1006) and a second branch (1008), and the measuring device (300) may be introduced into either branch of the connector (1004), advanced through the connector, and into the proximal end of the ET tube (1000).

Generally, the measuring devices described here may be used in conjunction with a connector, as the measuring device may be inserted into a first branch of the connector while a ventilator remains attached to the second branch, which may allow for ventilation of the patient during the measuring procedure. While a wye connector is described in the examples and illustrated in the figures, any suitable connector (e.g., wye, swivel) may be used with the measuring devices described here. It should be appreciated, however, that the measuring device may be used in the absence of a connector, although in some of these instances (depending on the nature of the ET tube and any connectors that may be attached to the ET tube) it may be necessary to temporarily disconnect the patient from the ventilator during measurement with the measuring device.

In some instances, the expandable stopper (306) may be sized such that the expandable stopper is larger than the proximal opening of the ET tube (1000) (or a connector attached thereto) when the expandable stopper is in an expanded configuration. Accordingly, it may be desirable to introduce the measuring device (300) into the ET tube (1000) with the expandable stopper (306) in a low-profile configuration. In some variations, this may comprise positioning the expandable stopper (306) within the lumen of the outer shaft (304). The lumen of the outer shaft (304) may constrain the expandable stopper (306) and may hold the expandable stopper (206) in a low-profile configuration, as is depicted in FIG. 10A.

Figure 10B:
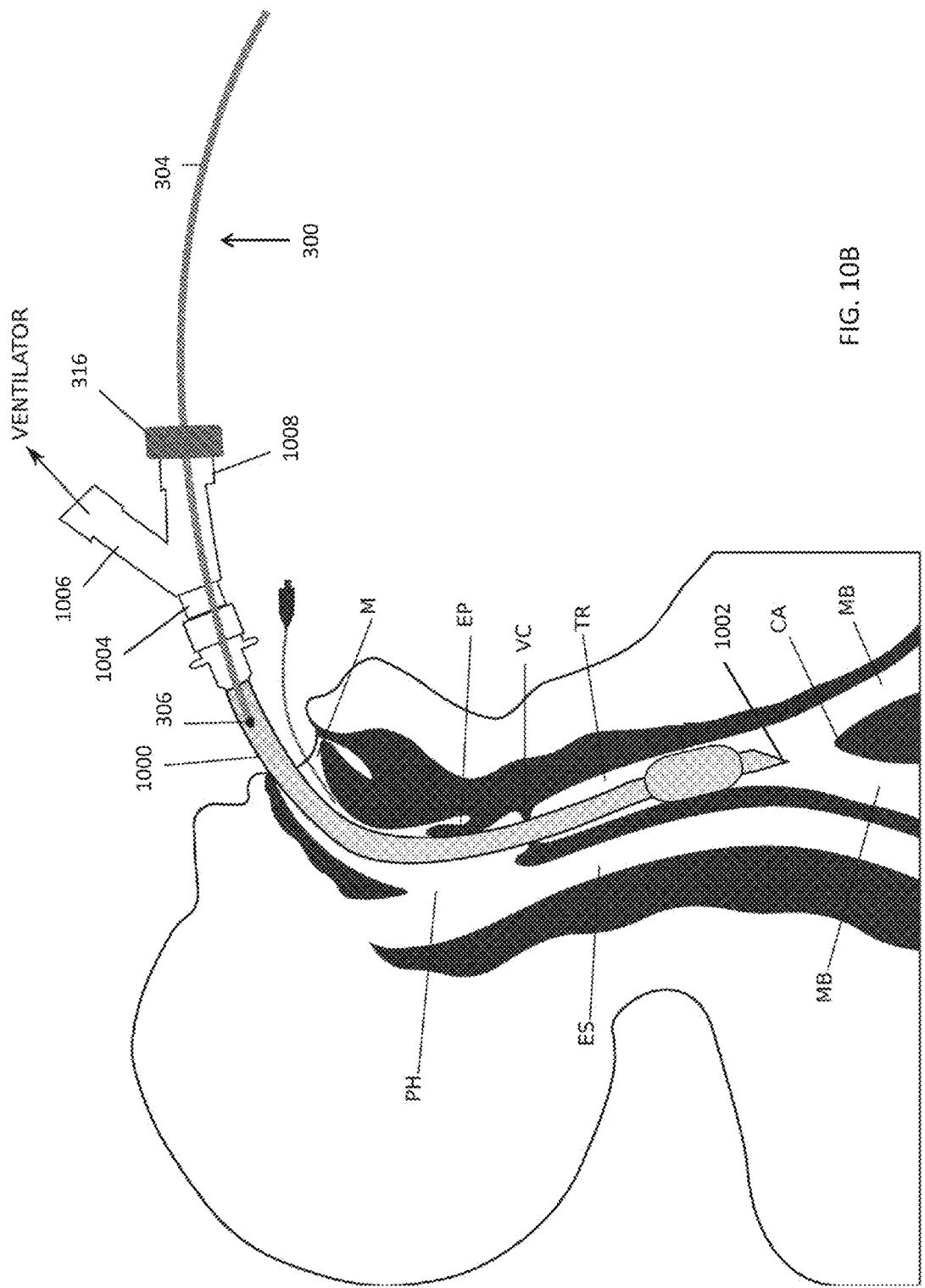

In some instances, once the measuring device (300) is introduced into the ET tube (1000), the opening through which the measuring device (300) is introduced may be sealed to prevent airflow therethrough. For example, as shown in FIG. 10B, a distal portion of the measuring device (300) may be introduced into the ET tube (1000) via a first branch (1008) of the connector (1004), and a ventilator (not shown) may be connected to the second branch (1006) of the connector (1004). As mentioned above, this may allow the patient to remain ventilated during the measuring procedure. Accordingly, to help prevent air pressure generated by the ventilator from escaping through the first branch (1008) of the connector (1004), it may be desirable to seal the opening of the first branch (1008) during use of the measuring device (300).

When an opening in an ET tube (1000) or connector is sealed as discussed above, this may be done in any suitable manner. In some variations, this may comprise advancing a securement mechanism or sealing member against the opening to block airflow therethrough. For example, as shown in FIG. 10B, the securement mechanism (316) may be advanced into contact with the opening of the first branch (1008) to cover the opening, which may in turn block airflow therethrough. In some variations, a securement mechanism or sealing member used to provide a seal may be temporarily connected to or may otherwise hold itself in place relative to the ET tube or connector to maintain the seal. For example, in some variations, a portion of the securement mechanism or sealing member may enter the ET tube or connector to create a friction or pressure fit therewith. Additionally or alternatively, the securement mechanism or sealing member may be configured to clip or clamp to the ET tube or connector.

Alignment

Once introduced into the ET tube (1000), the measuring device (300) may be advanced relative to the ET tube to create a desired alignment between the measuring device and the ET tube. In variations where the outer shaft (304) comprises one or more alignment markings (314), the measuring device (300) may be advanced to align the one or more alignment marking (314) with a portion of the ET tube (1000). Generally, the one or more alignment markings (314) are aligned with a portion of the ET tube (1000) that is a known distance from the distal tip (1002) of the ET tube. For example, in instances where the length of the ET tube (1000) is known, an alignment marking (314) may be aligned with the proximal tip of the ET tube (1000). In other variations, the ET tube may comprise one or more length markings along the length of the ET tube, as was discussed above, where each length marking represents a different distance from the distal tip (1002) of the ET tube (1000) (for example, ET tubes generally have length markings every 2 cm to indicate distance from the distal tip of the ET tube). In these variations, the one or more alignment markings (314) may be aligned with one or more specific length markings.

Figures 10C, 10D:
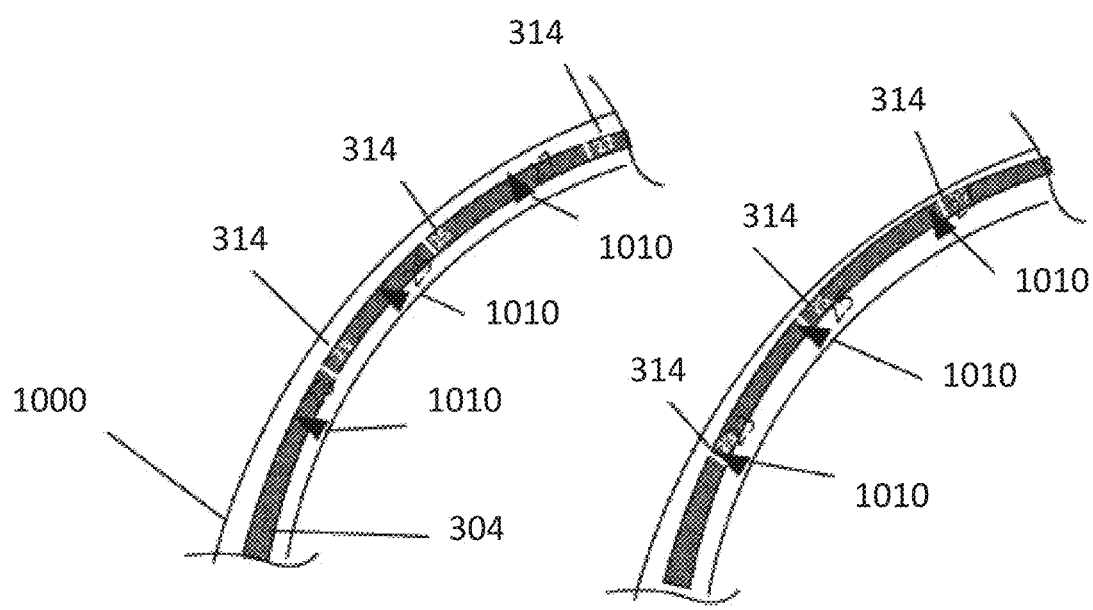

For example, as shown in FIGS. 10C and 10D, the ET tube (1000) may comprise a plurality of length markings (1010). Similarly, in the variation of measuring device shown in FIGS. 10C and 10D, the outer shaft (304) may comprise a plurality of alignment markings (314) which may correspond to some or all of the length markings (1010) of the ET tube. For example, as shown in FIGS. 10C and 10D, the ET tube (1000) may comprise three length markings (1010) labeled 23, 25, and 27 (these length markings may correspond to 23 cm, 25 cm, and 27 cm, respectively, from the distal tip of the ET tube). The outer shaft (304) is shown there as including three alignment markings (314) also labeled 23, 25, and 27. To align the outer shaft (304) with the ET tube (1000), the outer shaft may be advanced or retracted until the alignment markings (314) of the outer shaft (304) are aligned with the similarly-labeled length markings (1010) of the ET tube (1000). For the purposes of illustration, FIG. 10C shows the outer shaft (304) misaligned relative to the ET tube (1000), while FIG. 10D shows the outer shaft (304) aligned relative to the ET tube (300).

While shown in FIGS. 10C and 10D as having three length markings (1010) spaced 2 cm from each other, the ET tube (1000) may comprise any suitable number of length markings (1010) (e.g., one, two, three, four, or five or more length markings) spaced any suitable distance from each other (e.g., 1 cm between markings, 2 cm between markings, etc.). Similarly, the outer shaft (304) may have any number of alignment markings (314) which may be spaced any suitable distance from each other. In some variations, a single alignment marking may be used in conjunction with one or more length markings of an ET tube. In these variations, the alignment marking may be aligned with a specific length marking of the ET tube. For example, the alignment marking may be aligned with a length marking corresponding to 24 cm from the distal tip of the ET tube, and the alignment marking may be labeled 24 to remind the user which length marking should be used.

In some variations, the outer shaft (304) may optionally be sized such that when the one or more alignment markings (314) are aligned with the desired portion or portions of the ET tube (1000), the distal end of the outer shaft (304) is aligned with the distal tip (1002) of the ET tube. For example, in some variations, the alignment markings may be configured such that the distance between an alignment marking and the distal end of the outer shaft is the same length as the entire ET tube. In these variations, aligning the alignment marking with the proximal inlet of the ET tube may also align the distal end of the outer shaft with the distal tip of the ET tube. In other variations, the alignment marking may be configured such that the distance between an alignment marking and the distal tip of the outer shaft is a predetermined length (e.g., 20 cm). In these variations, the alignment marking may be aligned with a length marking on the ET tube corresponding to the predetermined length. For example, if the distance between the alignment marking and the distal end of the outer shaft is 20 cm, a user may align the alignment marking with a length marking on the ET tube corresponding to 20 cm in order to align the distal end of the outer shaft with the distal tip of the ET tube.

In some variations, once the alignment marking is aligned relative to the ET tube (e.g., relative to the proximal tip of the ET tube or relative to a length marking of the ET tube), it may be desirable to maintain the relative positioning between the outer shaft and the ET tube. In some variations, a user may hold the ET tube and the outer shaft to maintain the positioning. In other variations, the outer shaft may be temporarily coupled to the ET tube. For example, in variations where the measuring device comprises a securement mechanism, the securement mechanism may be used to temporarily fix the outer shaft relative to the ET tube, as was described above.

Measurement

With the outer shaft (304) aligned with the ET tube (1000) and fixed in position, the inner shaft (302) may be advanced relative to the outer shaft (304) to expose the expandable stopper (306) from the distal outlet (309) of the outer shaft and out of the distal tip of the ET tube. Once advanced out of the outer shaft (304), the expandable stopper (306) may be moved to an expanded configuration. In some variations, the expandable stopper (306) may self-expand once the expandable stopper (306) is no longer constrained by the lumen of the outer shaft (304). In other variations, the expandable stopper (306) may be manually expanded (e.g., using one or more expansion controls or the like).

Figure 10E:
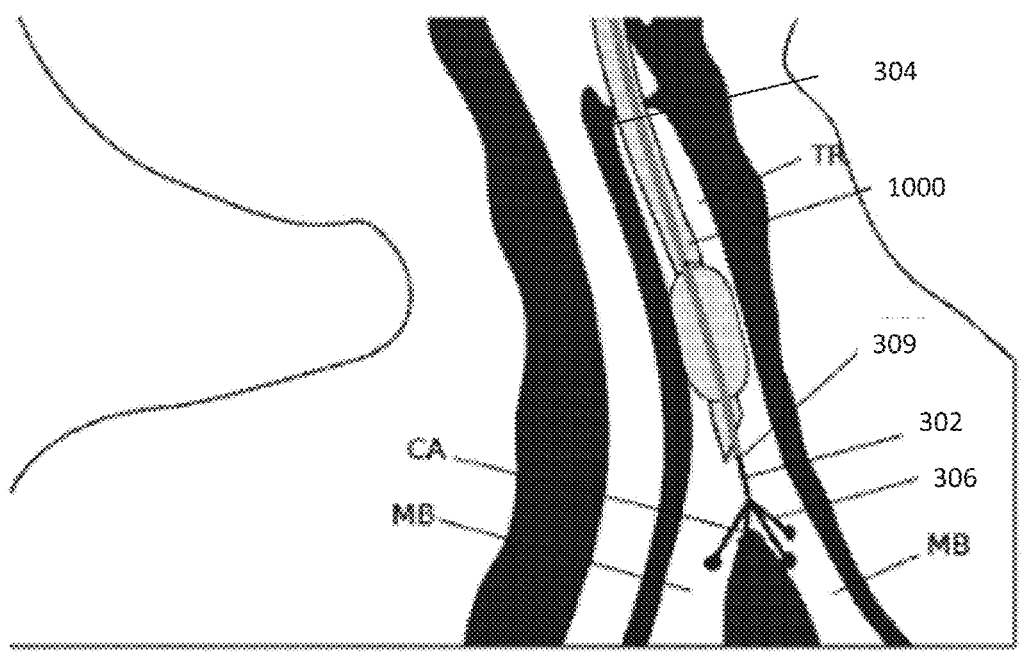

With the expandable stopper (306) expanded, the inner shaft (302) may be further advanced relative to the outer shaft (304) to advance the expandable stopper (306) along the trachea (TR) until the expandable stopper (306) reaches and engages the carina (CA), as shown in FIG. 10E. Generally, the expandable stopper (306) is configured such that upon reaching the carina (CA), the expandable stopper (206) engages the carina (CA) and resists further advancement past the carina (CA) and into either of the main bronchi (MB).

Once the expandable stopper (306) reaches the carina (CA), the relative positioning of one or more displacement markings on the inner shaft (302) and a portion of the outer shaft (304) may indicate the distance between the distal tip of the ET tube (1000) and the carina (CA). It should be appreciated that the one or more displacement markings (308) of the inner shaft (302) may be compared to any suitable portion of the outer shaft (304), as long as there is a known relationship between that portion of the outer shaft and the distal tip of the ET tube. The portions of the outer shaft that may be compared to displacement markings on an inner shaft include, but are not limited to, one or more alignment markings (314), the proximal inlet (307), or a window. FIG. 10G shows a variation of an outer shaft (304) that comprises a window (1012), which may be, for example, a transparent portion of the outer shaft in instances where the outer shaft is otherwise opaque, or may be a marked off section of a transparent outer shaft.

In some variations, the inner shaft (302) may comprise a single displacement marking (308). The displacement marking (308) may be configured such that the distance between the displacement marking (308) and a specific portion of the outer shaft (e.g., an alignment marking, the proximal inlet, a window) is the same as the distance between the expandable stopper (306) and the distal tip of the ET tube (1000). In these variations, the inner shaft (302) may be sized such that the alignment of the displacement marking (308) with the specific portion of the outer shaft (e.g., the alignment marking, the proximal inlet, the window) also aligns the expandable stopper (306) with the distal tip of the ET tube (1000) (while the outer shaft (304) is aligned with the ET tube (1000) such as discussed above). A user may advance the inner shaft (302) until the expandable stopper (306) reaches the carina (CA) and may measure the distance between the displacement marking (308) and the specific portion of the outer shaft (e.g., the alignment marking, the proximal inlet, the window) to determine the distance between the distal tip of the ET tube (300) and the carina (CA).

Figure 10F:
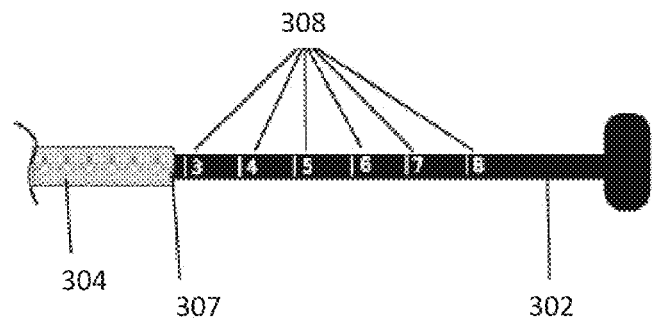
Figure 10G:
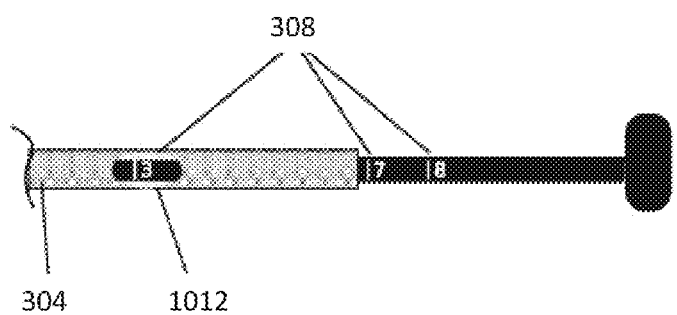

In other variations, the inner shaft may comprise a plurality of displacement markings, as is seen in FIGS. 10E-10H. In some variations, each displacement marking may correspond to a different distance between the expandable stopper and the distal tip of the ET tube (300), when that displacement marking is aligned with a specific portion of the outer shaft. In FIG. 10F, the specific portion of the outer shaft is the proximal inlet (307), in FIG. 10G it's a window (1012), and in FIG. 10H it's an alignment marking (314). However, the specific portion of the outer shaft that may be compared to displacement markings on the inner shaft may be any suitable portion of the outer shaft. In these variations, a user may advance the inner shaft (302) relative to the outer shaft (304) and ET tube (1000) until the expandable stopper engages the carina (CA). The user may then look at which displacement marking (308) is aligned (or most closely aligned) with the specific portion of the outer shaft (e.g., the alignment marking (314), the proximal inlet (307), the window (1012)), which may represent the distance between the distal tip of the ET tube (1000) and the carina (CA). For example, as shown in FIGS. 10E-10H, the displacement markings (208) may be labeled 0 through 8, and may each be separated by 1 cm. When the displacement marking (208) labeled 0 is aligned with the specific portion of the outer shaft (e.g., the alignment marking (314), the proximal inlet (307), the window (1012)), the expandable stopper may be aligned with a distal tip of the ET tube (1000). If the inner shaft is advanced 1 cm relative to the outer shaft (304) and the ET tube (300), the displacement marking labeled 1 may be aligned with the specific portion of the outer shaft (e.g., the alignment marking (314), the proximal inlet (307), the window (1012)) and the expandable stopper (306) may be 1 cm away from the distal tip of the ET tube (1000). Accordingly, when the expandable stopper (306) engages the carina, the displacement marking currently aligned with the specific portion of the outer shaft (e.g., the alignment marking (314), the proximal inlet (307), the window (1012)) may indicate the distance between the carina and the distal tip of the ET tube (300).

Figure 10H:
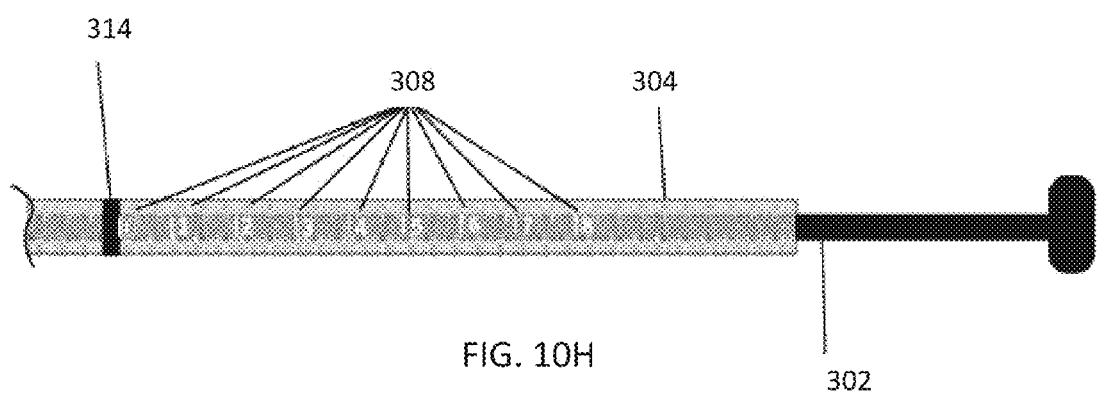

In the variation shown in FIG. 10H, the displacement marking (308) on the inner shaft labeled 0 is aligned with an alignment marking (314) on the outer shaft. This may indicate that the expandable stopper is aligned with the distal tip of the ET tube. In FIGS. 10F and 10G, the displacement marking (308) labeled 3 is aligned with the proximal inlet (307) of the outer shaft and a window (1012) of the outer shaft, respectively. These may indicate that the distal stopper has been advanced 3 cm distal to the distal tip of the ET tube.

In variations where a measuring device does not comprise an outer shaft, the measuring device may measure a distance between an expandable stopper and a distal tip of an ET tube by using a relative positioning of an elongate shaft of the measuring device and a portion of the ET tube (or a connector thereof). For example, with the measuring device (900) described above with respect to FIG. 9, the elongate shaft (902) may be advanced in the trachea until the expandable stopper (904) engages the carina. With the expandable stopper (904) engaging the carina, the relative position of the one or more elongate shaft markings (906) and the ET tube may indicate the distance between the distal tip of the ET tube and the carina. This distance may be determined by comparing the relative positioning of the one or more markings (906) and any suitable portion of the ET tube, so long as the relationship with the distal tip of the ET tube is known. Suitable portions of the ET tube may include, but are not limited to, a length marking on the ET tube, a proximal end of the ET tube, or a proximal end of a connector attached to an ET tube.

ET Tube Positioning

The measuring devices described here may also be used to help position an ET tube relative to tissue. In some instances, the measuring devices may be used to reposition an ET tube after the patient has been intubated. In other instances, a measuring device may be used during intubation of a patient (e.g., to help prevent the ET tube from being advanced past the carina during intubation and/or to position the ET tube a predetermined distance from the carina).

Repositioning an ET Tube

To reposition an existing ET tube relative to the carina using a measuring device with displacement markings on an inner shaft as described here, the measuring device may first be used to measure the distance between the carina and the ET tube as described above with respect to FIGS. 10A-10H. Specifically, an outer shaft of the measuring device (e.g., the outer shaft (304) of the measuring device (300) described above with respect to FIG. 3) may be aligned relative to the ET tube to align one or more alignment markings of the outer shaft with a specific portion or portions of the ET tube (e.g., a proximal tip of the ET tube or a length marking of the ET tube, as discussed above). An inner shaft (e.g., the inner shaft (302)) may be advanced relative to the outer shaft to advance an expandable stopper (e.g., the expandable stopper (306)) into engagement with the carina. With the expandable stopper engaging the carina, the relative positioning between one or more displacement markings of the inner shaft and either the outer shaft (e.g., an alignment marking of the outer shaft) or the ET tube may indicate the distance between the carina and the distal tip of the ET tube, as discussed above.

If this measured distance between the distal tip of the ET tube and the carina is greater than the desired separation distance (e.g., greater than 5 cm), the ET tube and the outer shaft of the measuring device may be advanced toward the carina until the desired separation distance is achieved. In some of these variations, the inner shaft may be held in place with the expandable stopper engaging the carina, and the ET tube and outer shaft may be advanced until the displacement marking aligned with a specific portion of the outer shaft (e.g., an alignment marking) or ET tube indicates that the desired distance has been reached. In others of these variations, the inner shaft may be withdrawn relative to ET tube and the outer shaft until the expandable stopper is positioned a distance from the ET tube that corresponds to the desired separation distance (e.g., as indicated by the alignment of an alignment marking on the outer shaft with a displacement marking on the inner shaft). The ET tube, inner shaft, and outer shaft may then be advanced together until the expandable stopper reengages the carina. Conversely, if the measured distance is smaller than the desired separation distance, the outer shaft and the ET tube may be withdrawn relative to the inner shaft until the distance between the ET tube and the carina reaches the desired distance (e.g., as indicated by the alignment of an alignment marking on the outer shaft and a displacement marking on the inner shaft).

Positioning an ET Tube During Intubation

FIGS. 11A-11D depict two different methods by which a measuring device as described here may be used during intubation to help position an ET tube relative to the carina of a patient. For the purposes of illustration, the measuring device (300) described above with respect to FIG. 3 is shown in FIGS. 11A-11D to facilitate placement of an ET tube (1100) relative to the carina (CA) (the anatomical structures are labeled the same as in FIG. 1), but it should be appreciated that any measuring device described here with displacement markings on the inner shaft may be used for the methods described here.

Figure 11A:
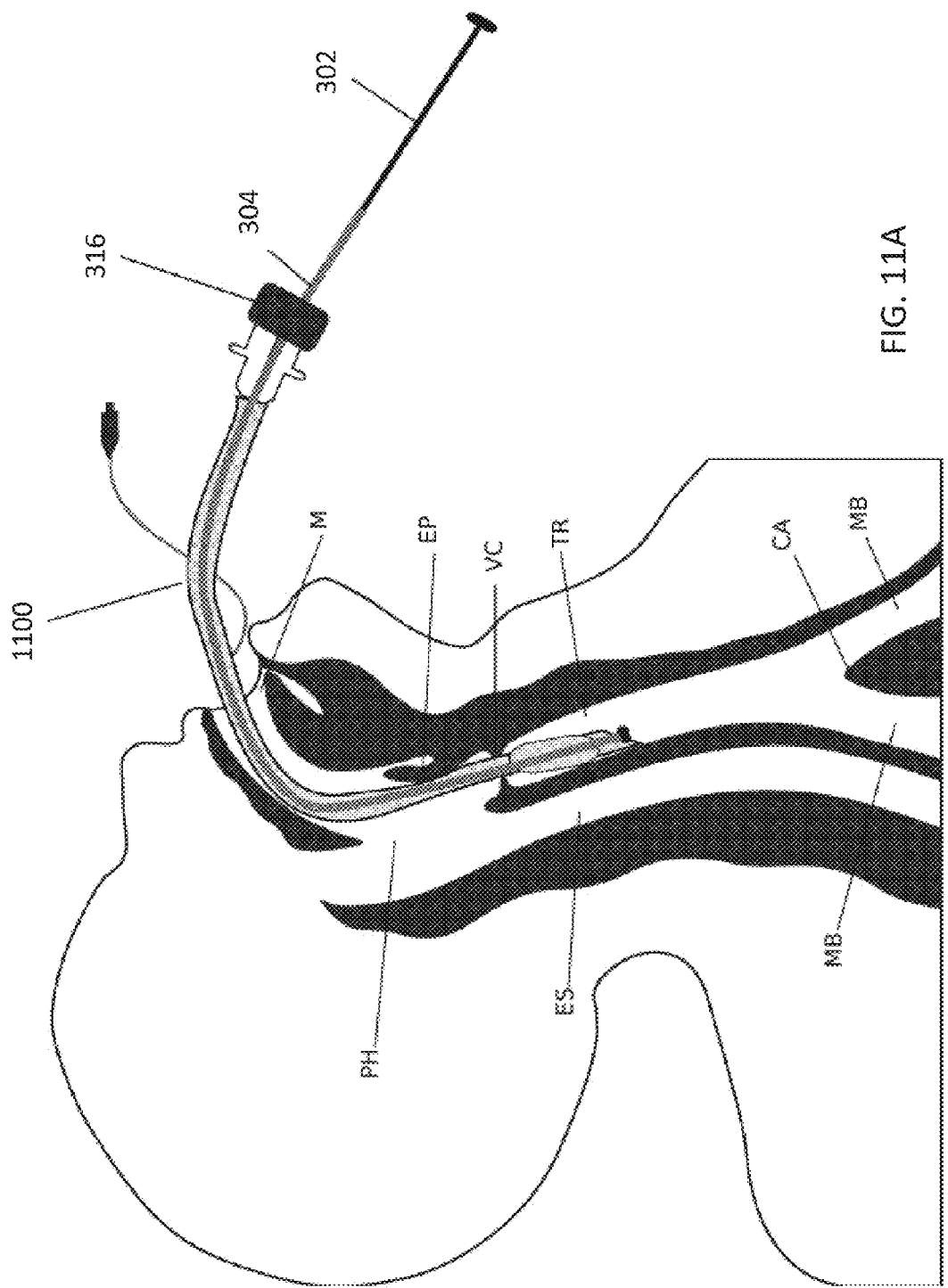

Initially, as shown in FIG. 11A, the ET tube (1100) is advanced and positioned such that a distal tip of the ET tube is in the trachea (TR) past the vocal cords (VC) (preferably less than three centimeters past the vocal cords (VC)), and the measuring device (300) is positioned within the ET tube (1100). In some variations, the ET tube (1100) is first positioned as shown in FIG. 11A, and the measuring device (300) is then advanced into the ET tube (1100) (e.g., through a proximal end of the ET tube or a connector attached thereto). In other instances, the measuring device (300) may be advanced into the ET tube (1100) prior to introduction of the ET tube, and the ET tube and measuring device may be advanced together.

In some variations, the outer shaft (304) of the measuring device (300) may be shapeable (e.g., may be made from a malleable metal such as aluminum) to allow the outer shaft to act as a shapeable stylet during intubation. In these variations, the outer shaft (304) may be shaped to comprise one or more bends or curves, which may change the shape of the ET tube (1100) when the outer shaft is positioned in the ET tube. The outer shaft (304) may be inserted into the ET tube (1100) to reshape the ET tube, and the outer shaft (304) and ET tube (1100) may be advanced together to intubate the patient. Additionally or alternatively, a separate stylet may be inserted into the ET tube (1100) with the measuring device (300) to facilitate intubation.

Either before or after placement of the distal tip of the ET tube (1100) in the trachea (TR) past the vocal cords (VC), the outer shaft (304) of the measuring device (300) may be advanced relative to the ET tube to align an alignment marking (314) of the outer shaft relative to a predetermined location of the ET tube (e.g., a proximal tip of the ET tube or a length marking of the ET tube, as discussed above). As discussed previously, in some instances this may align the distal end of the outer shaft (304) with the distal tip of the ET tube (1100). In variations where the measuring device (300) comprises a securement mechanism (316), the securement mechanism may temporarily fix the outer shaft (304) relative to the ET tube (1100).

Figure 11B:
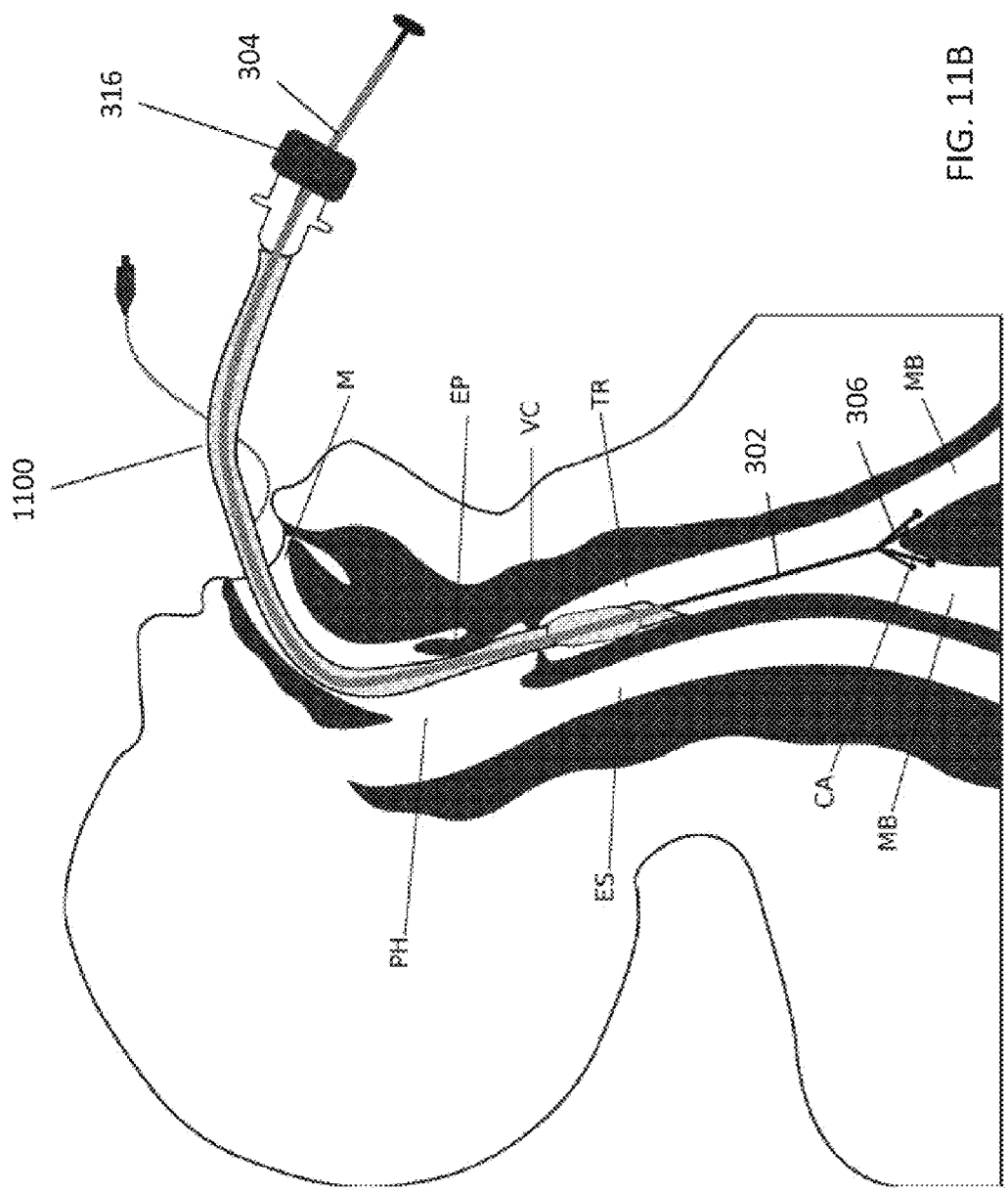

With the outer shaft (304) aligned relative to the ET tube (1100), the inner shaft (302) may be advanced relative to the outer shaft and the ET tube to advance the expandable stopper (306) from the distal ends of the outer shaft and the ET tube. The expandable stopper (306) may be expanded to an expanded configuration, such as described above. In some variations, with the expandable stopper (306) expanded, the inner shaft (302) may be advanced relative to the outer shaft (304) and the ET tube (1100) to advance the expandable stopper (306) until it engages the carina (CA), as shown in FIG. 11B. With the expandable stopper (306) engaging the carina (CA), a user may determine the distance between the distal tip of the ET tube (1100) and the carina (CA) using the relative positioning between the one or more displacement markings (308) of the inner shaft (302) and the outer shaft or the ET tube, as described in more detail above. The outer shaft (304) and the ET tube (1100) may be advanced together until the separation distance between the ET tube (1100) and the carina (CA) is the desired distance, such as shown in FIG. 4C.

Figure 11D:
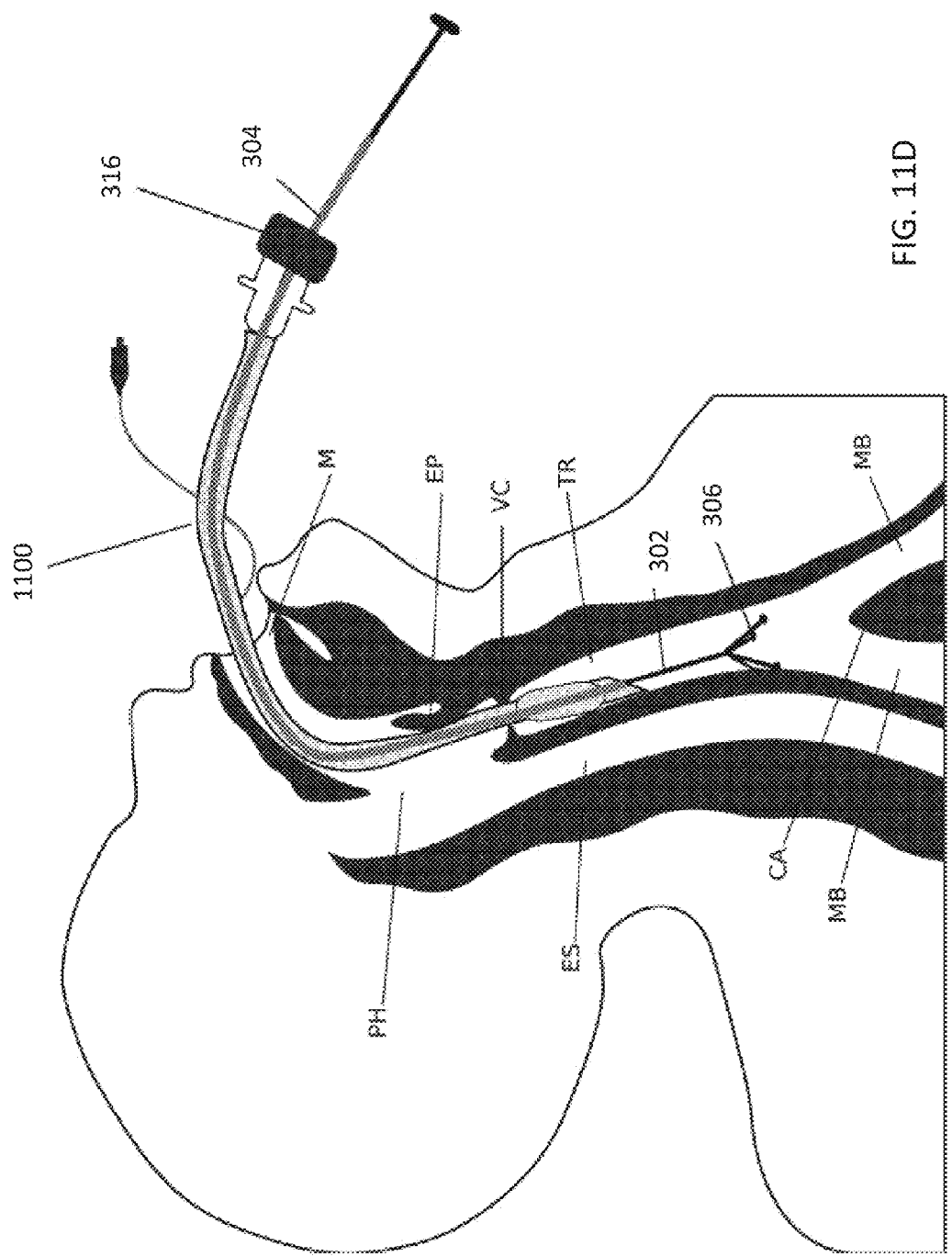

In other variations, the expandable stopper (306) may be advanced until the distance between the expandable stopper and the distal tip of the ET tube (1100) (e.g., as measured by the relative positioning between the one or more displacement markings (308) and the outer shaft (304) or ET tube (1100)) is the same as the desired separation distance between the distal tip of the ET tube and the carina (CA), such as depicted in FIG. 11D. In these variations, the ET tube (1100), inner shaft (302) and the outer shaft (304) may be advanced together until the expandable stopper (306) engages the carina (CA), which may position the ET tube (1100) the desired separation distance from the carina (CA), such as shown in FIG. 11.

It should be appreciated that in some instances, the patient may receive ventilation from the ET tube (1100) during positioning of the ET tube using the above method. For example, in some variations of the ET tube (1100), a wye connector (not shown) may be attached to the ET tube. In these variations, the measuring device (300) may be introduced into the ET tube (1100) through a first branch of the wye connector, and a ventilator may be connected to the second branch to provide ventilation therethrough during the positioning steps. In some of these variations, a securement mechanism or sealing member may seal the first branch of the wye connector to prevent airflow therethrough.

Variation of Device with Numerical Alignment and Displacement Markings on the Outer Shaft In the variations of the measuring device described here, there may not be position markings positioned on the inner shaft, as was described in variations above. As shown in FIGS. 2A and 2B, and in detail in FIGS. 12A and 12B, the outer shaft (204) may comprise one or more alignment markings (214) and one or more displacement markings (208). In variations of the measuring device that comprise an alignment sheath (240), one or more of these markings may be positioned on the alignment sheath (240). Generally, an alignment marking (214) may be aligned with one or more portions of an ET tube to set an initial relationship between the positioning of the outer shaft (204) and the ET tube. When the outer shaft (204) is moved away from the initial relationship with the ET tube (e.g., when the outer shaft (204) is advanced relative to the ET tube), the displacement markings (208) may be used to measure the amount of displacement from the initial relationship.

Figure 12A:
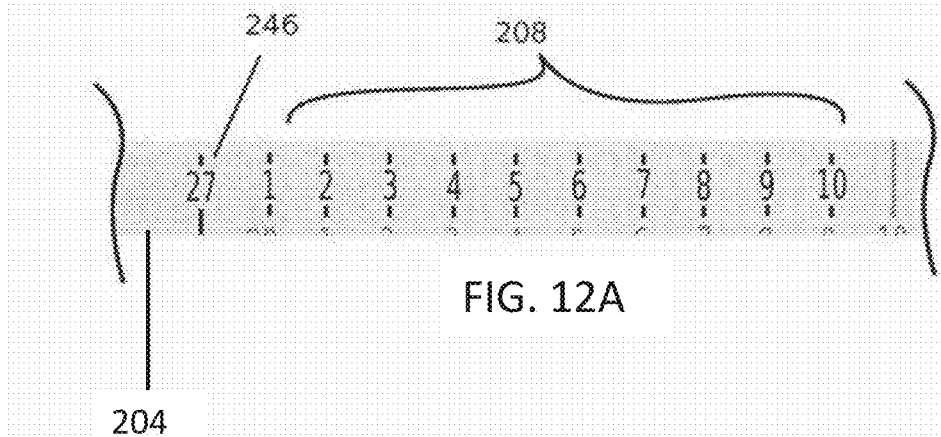
FIGS. 12A and 12B depict variations of alignment and displacement markings of the measuring devices described here.
Figure 12B:
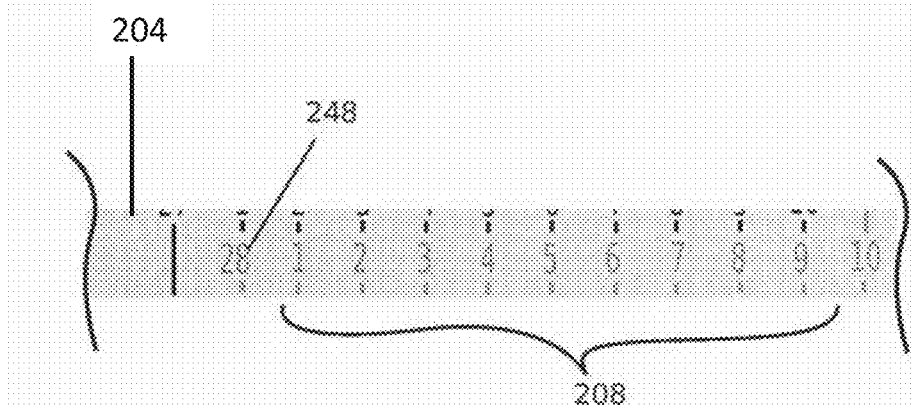

In some variations, such as shown in FIGS. 12A and 12B, the outer shaft (204) may comprise a first alignment marking (246) and a second alignment marking (248). The first alignment marking (246) may be configured for alignment with an odd length marking of an ET tube and a second alignment marking (248) may be configured for alignment with an even length marking of an ET tube (or vice versa), which may allow the outer shaft to be aligned with an ET tube regardless of whether the ET tube has even or odd length markings. The measuring device (200) can be rotated relative to the ET tube to align the desired alignment marking with a length marking of the ET tube. While the first alignment marking (246) and second alignment marking (248) are shown in FIGS. 12A and 12B as being configured to align with 27 cm and 28 cm length markings of an ET tube, respectively, (the first alignment markings (246) may be labeled "27" or "27 cm" and the second alignment marking (248) may be labeled "28" or "28 cm" in these instances) these may be configured to align with any length markings between 10 cm and 35 cm. In some variations, these alignment markings may be configured to align with any length markings between 20 cm and 30 cm. In other variations, these alignment markings may be configured to align with any length markings between 10 cm and 20 cm.

The alignment markings may be configured to align one or more portions of the measuring device (200) with one or more portions of the ET tube when the alignment marking is aligned with a corresponding length marking on the ET tube. For example, in some variations, the distal end of the outer shaft (204) may be aligned with the distal tip of the ET tube when an alignment marking is aligned with a corresponding length marking (e.g., when the first alignment marking (246) is aligned with the 27 cm length marking of the ET tube). In other variations, when an alignment marking is aligned with a corresponding length marking and the inner shaft (202) is advanced relative to the outer shaft (204) such that the handle (212) contacts the cap (242) (such as shown in FIG. 2A), the expandable stopper (206) may be aligned with a distal tip of the ET tube. In these variations, the portion of the expandable stopper that may be aligned with the distal tip of the ET tube may be the portion of the expandable stopper that may engage or catch the carina (e.g., the vertex of a plurality of prongs, the distal end of solid foam structure).

Each of the first alignment marking (246) and the second alignment marking (248) may have a set of displacement markings (208) associated with the respective alignment marking. Each displacement marking (208) may indicate a distance between that displacement marking (208) and the respective alignment marking. After the alignment marking is aligned with the ET tube to set an initial relationship (as discussed above), any further advancement of the outer shaft (204) may align one of the displacement markings (208) with the ET tube length marking that was used for alignment. In variations where alignment aligns the distal end of the outer shaft and/or the expandable stopper with the distal tip of the ET tube, the displacement marking (208) may indicate the distance the outer shaft (204) and/or the expandable stopper has been advanced past the distal tip of the ET tube. While each of the first and second alignment markings are shown in FIGS. 12A and 12B as having ten associated displacement markings (208), it should be appreciated that each alignment marking may have any quantity of displacement markings (e.g., between 1 and 20 displacement markings).

Figure 13A:
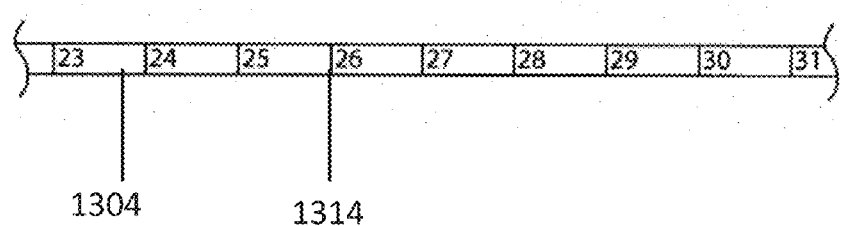
FIG. 13A depicts a variation of alignment markings of the measuring devices described here.
Figures 13B, 13C:
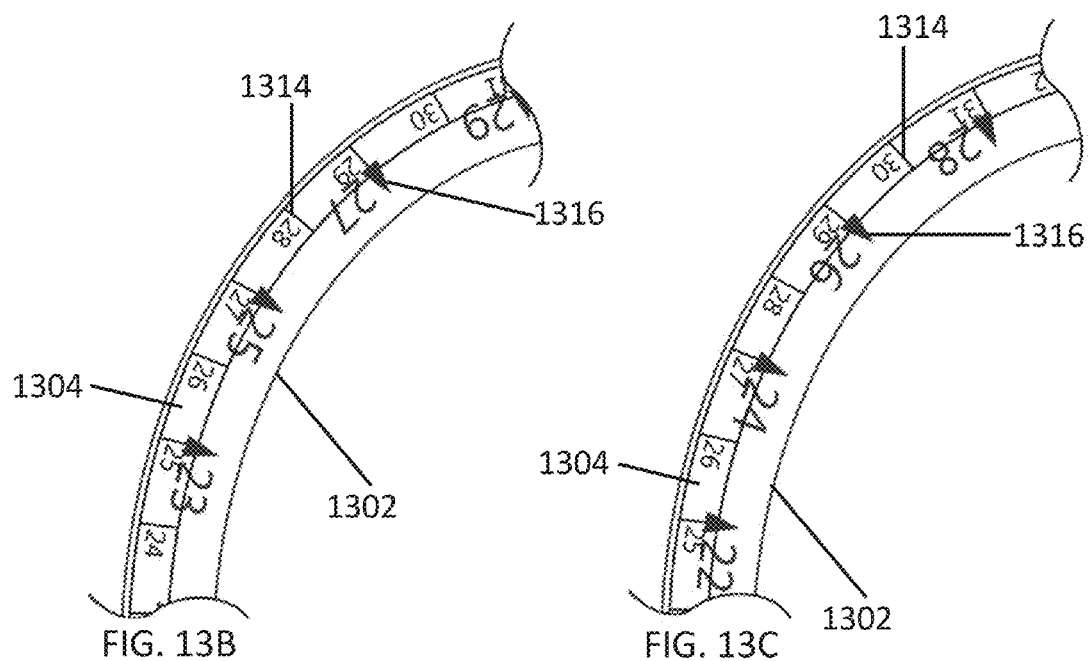
FIGS. 13B and 13C depict variations of methods by which the alignment markings of FIG. 13A may be used to measure a distance in an airway of an intubated patient.

As shown in FIG. 13A, in another variation of the measuring device, the outer shaft (1304) may comprise a plurality of alignment markings (1314) without displacement markings, each alignment marking representing a 1 cm increment (e.g., 24, 25, . . . , 40). The alignment markings may facilitate alignment with odd-numbered ET tubes as well as even-numbered ET tubes. This alignment may indicate that the distal end of the measuring device is aligned with the distal tip of the ET tube (1302), as was described above. The distance the device is advanced relative to the ET tube (1302) may be determined by calculating the difference between an outer shaft displacement marking (1314) and the nearest ET tube length marking (1316). For example, FIG. 13B shows a device advancement of 2 cm in an odd-numbered ET tube. As another example, FIG. 13C shows a device advancement of 3 cm in an even-numbered ET tube.

Measurement Methods

As mentioned above, the measuring devices described here may be used to measure a distance in the airway. For example, in some variations, the measuring device may be used to measure a distance between an ET tube (e.g., a distal tip of the ET tube) and the carina. This may allow a user or practitioner to determine the positioning of the ET tube in a patient's airway, and to reposition the ET tube if necessary. In some instances, the measuring device may be used to aid in placement of the ET tube. FIGS. 14A-14D depict a method by which the measuring devices described here, with numerical alignment and displacement markings on the outer shaft, may be used to determine the position of an ET tube relative to the carina. For the purposes of illustration, the measuring device (200) described above with respect to FIGS. 2A and 2B is shown in FIGS. 14A-14D to measure a distance between the ET tube (1400) and the carina (CA).

The various methods of introducing the measuring device into the ET tube are the same as those described above for variations of the device comprising displacement markings on the inner shaft.

Alignment

Once introduced into the ET tube (1400), the measuring device (200) may be advanced relative to the ET tube (1400) to create a desired alignment between the measuring device (200) and the ET tube (1400). In variations where the outer shaft (204) comprises one or more alignment markings (214), the measuring device (200) may be advanced to align the one or more alignment marking (214) with a portion of the ET tube (1400). Generally, the one or more alignment markings (214) may be aligned with a portion of the ET tube (1400) that is a known distance from the distal tip (1402) of the ET tube. For example, in instances where the length of the ET tube (1400) is known, an alignment marking (214) may be aligned with the proximal tip of the ET tube (1400). In other variations, the ET tube may comprise one or more length markings (1410) along the length of the ET tube, where each length marking represents a different distance from the distal tip of the ET tube (1400) (for example, ET tubes generally have length markings every 2 cm to indicate distance from the distal tip of the ET tube, as was discussed above). In these variations, the one or more alignment markings (214) may be aligned with one or more specific length markings (1410) on the ET tube (1400).

Figure 14A:
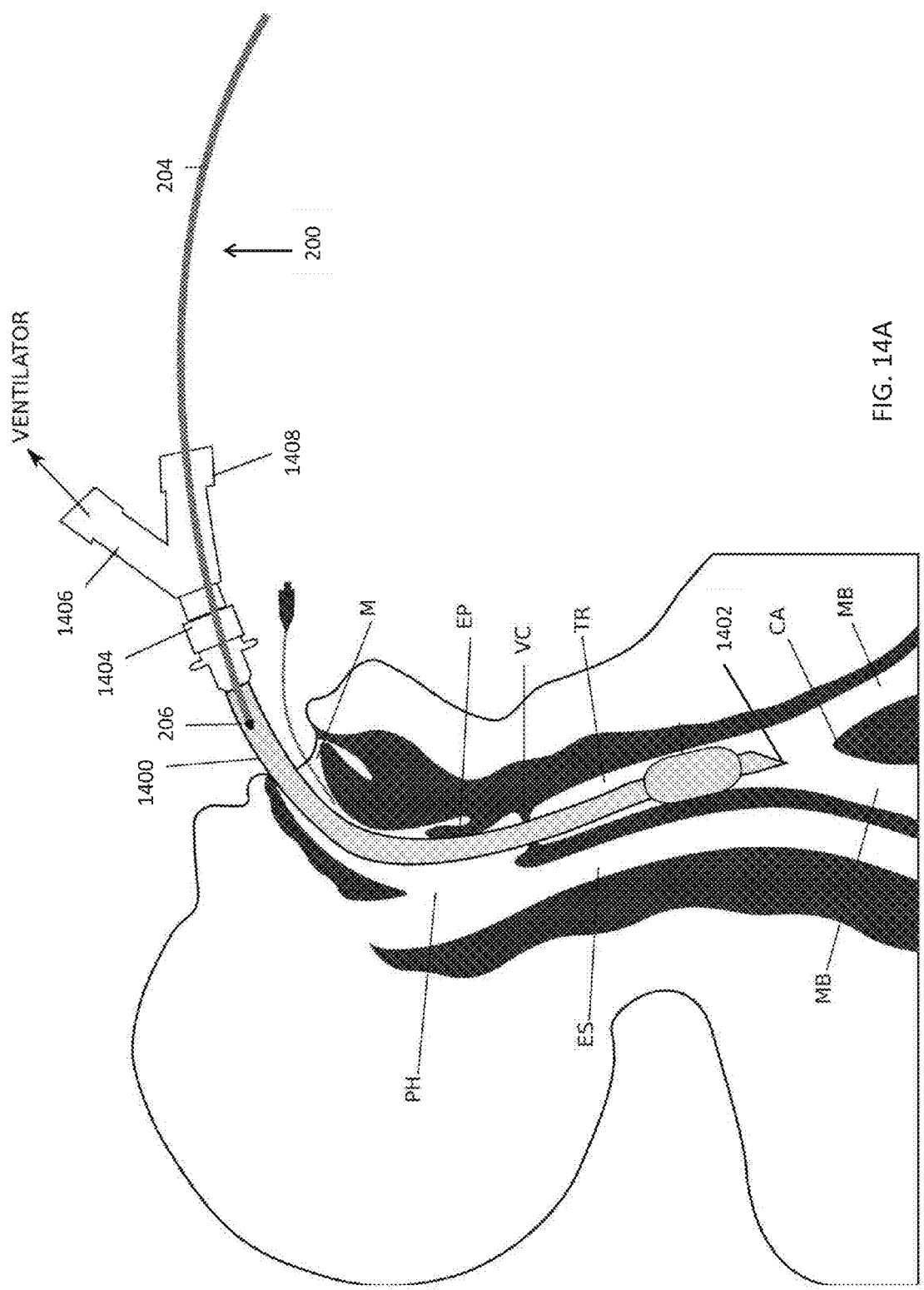
FIGS. 14A-14D depict variations of methods by which a measuring device described here may be used to measure a distance between a distal tip of an ET tube and the carina of an intubated patient.
Figures 14B, 14C:
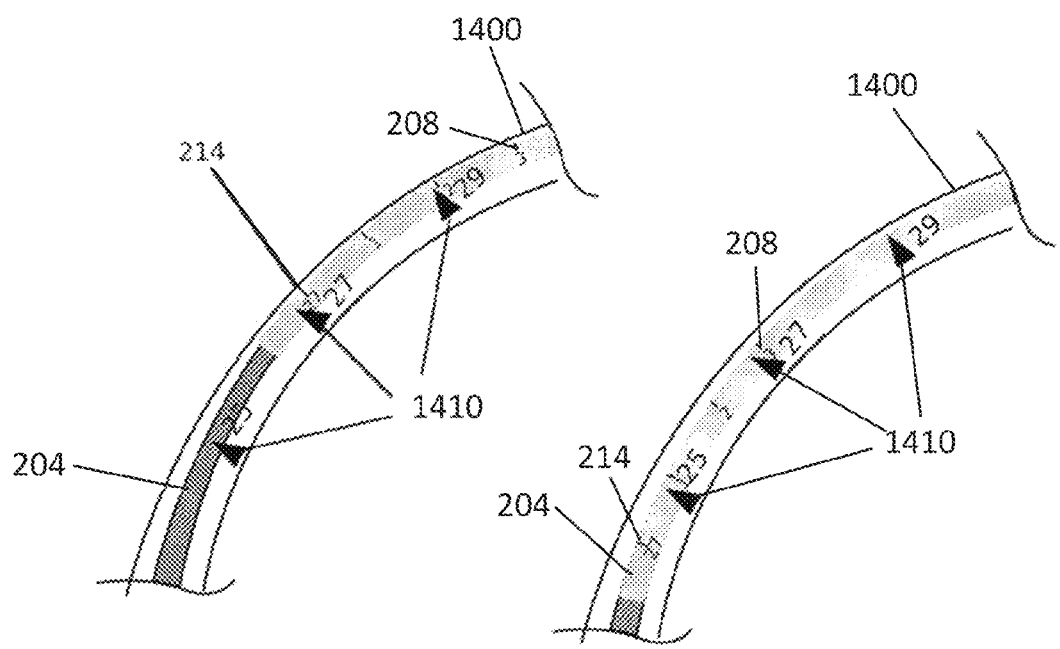

For example, as shown in FIGS. 14B and 14C, the ET tube (1400) may comprise a plurality of length markings (1410). As shown in FIG. 14B, the outer shaft (204) may be advanced relative to the ET tube (1400) to align the alignment marking (214) with a specific length marking (1410) of the ET tube. For example, as shown in FIG. 14B, the ET tube (1400) may comprise three length markings (1410) labeled 25, 27, and 29 (these length markings may correspond to 25 cm, 27 cm, and 29 cm, respectively, from the distal tip of the ET tube). To set the initial alignment between the outer shaft (204) and the ET tube (1400), the outer shaft (204) may be advanced or retracted until the alignment marking (214) of the outer shaft (204) is aligned with the similarly-labeled length marking (1410) of the ET tube (1400). For example, as shown in FIG. 14B, an alignment marking (214) may be configured to align with the 27 cm length marking (1410) of the ET tube (1400).

Figure 15A:
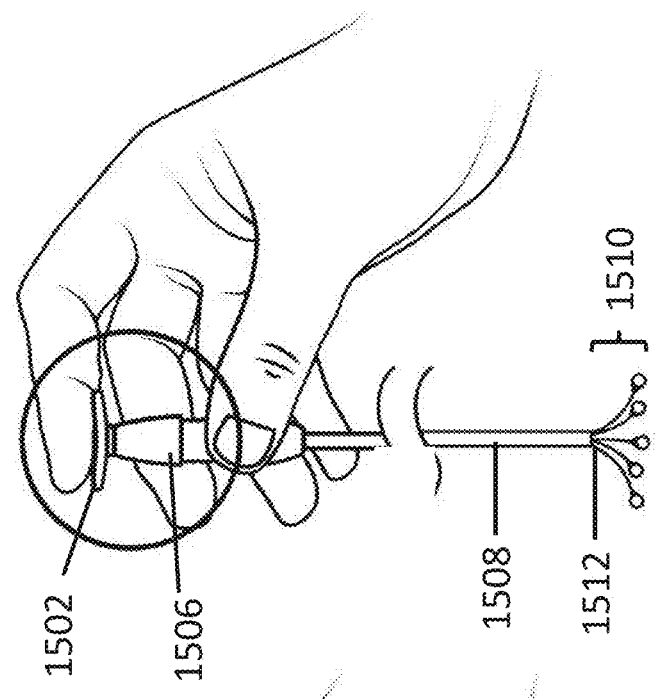
FIGS. 15A and 15B depict a variation of a portion of a method of using the measuring devices described here.
Figure 15B:
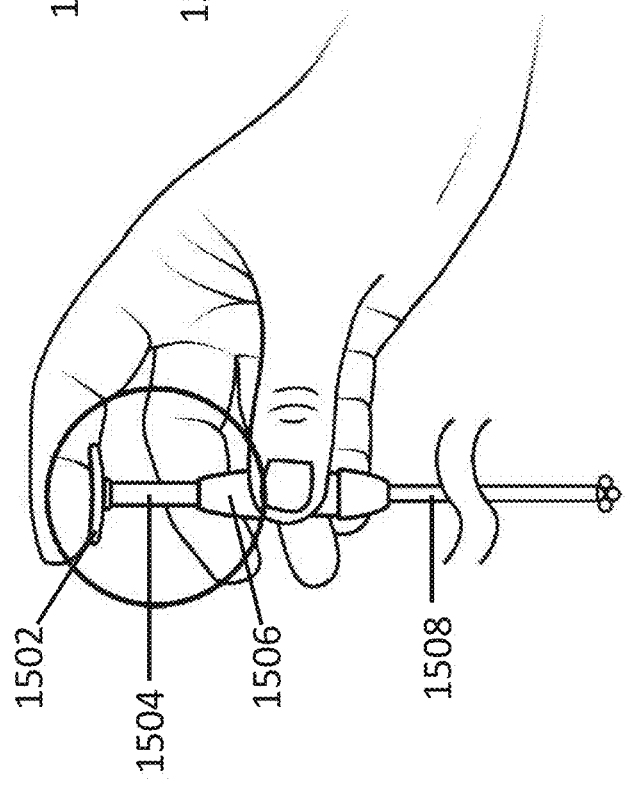

In some variations, the outer shaft (204) may optionally be sized such that when the one or more alignment markings (214) are aligned with the desired portion or portions of the ET tube (1400), the distal end of the outer shaft (204) is aligned with the distal tip of the ET tube (1400). For example, in some variations, the alignment marking (214) may be configured such that the distance between the alignment marking and the distal end of the outer shaft (204) is a predetermined length (e.g., 27 cm). In these variations, the alignment marking (214) may be aligned with a length marking (1410) on the ET tube (1400) corresponding to the predetermined length. For example, if the distance between the alignment marking (214) and the distal end of the outer shaft (204) is 27 cm, a user may align the alignment marking with a length marking (1410) on the ET tube (1400) corresponding to 27 cm to align the distal end of the outer shaft with the distal tip of the ET tube. In some variations, following alignment of the distal end of the outer shaft with the distal tip of the ET tube, a user may expand the expandable stopper at the distal end of the inner shaft by advancing the inner shaft relative to the outer shaft. As shown in FIGS. 15A and 15B, this expansion of the expandable stopper (1510) may be accomplished by moving a cap (1502) at the proximal end of the inner shaft (1504) toward a handle (1506) at the proximal end of the outer shaft (1508). In some variations, this may align the expandable stopper (1510) with the distal tip of the ET tube. In these variations, the portion of the expandable stopper that may be aligned with the distal tip of the ET tube may be the portion of the expandable stopper that may engage or catch the carina (e.g., the vertex (1512) of a plurality of prongs, the distal end of solid foam structure).

Measurement

With the outer shaft (204) aligned with the ET tube (1400), the inner shaft (202) may be advanced relative to the outer shaft (204) to expose the expandable stopper (206) from the distal outlet (209) of the outer shaft (204) and out of the distal tip of the ET tube. Once advanced out of the outer shaft (204), the expandable stopper (206) may be moved to an expanded configuration. In some variations, the expandable stopper (206) may self-expand once the expandable stopper (206) is no longer constrained by the lumen of the outer shaft (204). In other variations, the expandable stopper (206) may be manually expanded (e.g., using one or more expansion controls or the like).

Figure 14D:
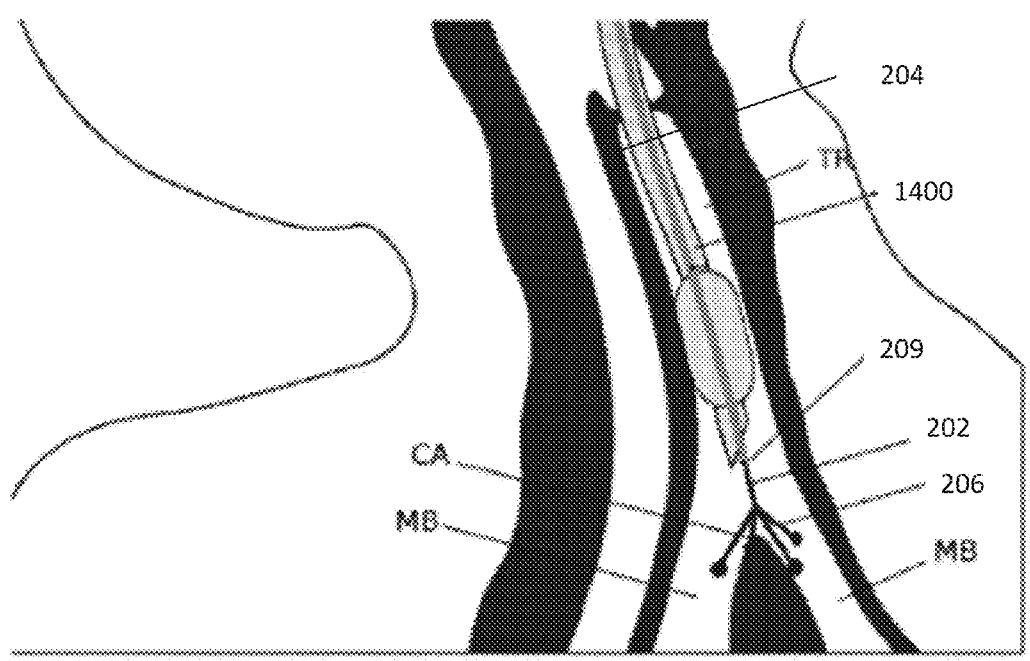

With the expandable stopper (206) expanded, the measuring device may be further advanced relative to the ET tube to advance the expandable stopper (206) along the trachea (TR) until the expandable stopper (206) reaches and engages the carina (CA), as shown in FIG. 14D. Generally, the expandable stopper (206) is configured such that upon reaching the carina (CA), the expandable stopper (206) engages the carina (CA) and resists further advancement past the carina (CA) and into either of the main bronchi (MB).

Once the expandable stopper (206) reaches the carina (CA), the relative positioning between the displacement markings (208) on the outer shaft (204) and the ET tube (300) may be used to determine the distance between distal tip of the ET tube (1400) and the carina (CA). Generally, a user may determine this distance using the displacement marking (208) most closely positioned to the length marking (1410) on the ET tube that was used during initial alignment, as was described in more detail above. In the example shown in FIG. 14C, the measuring device has been advanced 3 cm past the distal tip of the ET tube, as indicated by the alignment of the displacement marking (208) labeled 3 with the length marking (1410) that was used for alignment (the length marking labeled 27).

ET Tube Positioning

The measuring devices described here may also be used to help position an ET tube relative to tissue. In some instances, a measuring device may be used to reposition an ET tube after the patient has been intubated. In other instances, a measuring device may be used during intubation of a patient (e.g., to help prevent the ET tube from being advanced past the carina during intubation and/or to position the ET tube a predetermined distances from the carina).

Repositioning an ET Tube

For example, to reposition an ET tube relative to the carina using a measuring device as described here with alignment and displacement markings on the outer shaft, the measuring device may first be used to measure the distance between the carina and the ET tube as described above with respect to FIGS. 3A-3D. Specifically, an outer shaft (204) of the measuring device (200) described above with respect to FIG. 2A may be aligned relative to the ET tube to align one or more alignment markings of the outer shaft with a specific portion or portions of the ET tube (e.g., a proximal tip of the ET tube or a length marking of the ET tube, as discussed above). An inner shaft (e.g., the inner shaft (202)) may be advanced relative to the outer shaft to advance an expandable stopper (e.g., the expandable stopper (206)). The entire measuring device may then be advanced until the expandable stopper engages the carina. With the expandable stopper engaging the carina, the relative positioning between one or more displacement markings of the outer shaft (e.g., a displacement marking of the outer shaft (204)) and a portion of the ET tube (e.g., a proximal tip of the ET tube or a length marking of the ET tube) may indicate the distance between the carina and the distal tip of the ET tube, as discussed above.

If this measured distance between the carina and distal tip of the ET tube is greater than the desired distance (e.g., greater than 5 cm), the ET tube may be advanced toward the carina until the desired distance is achieved. In some of these variations, the measuring device may be held in place with the expandable stopper engaging the carina, and the ET tube may be advanced until the desired distance has been reached (e.g., as indicated by the displacement marking on the outer shaft that is closest to the length marking on the ET tube that was used during alignment). In others of these variations, the measuring device may be withdrawn relative to the ET tube until the expandable stopper is positioned a distance from the distal tip of ET tube that corresponds to the desired separation distance (e.g., as indicated by the displacement marking on the outer shaft that is closest to the length marking on the ET tube that was used during alignment). The ET tube and measuring device may then be advanced together until the expandable stopper reengages the carina. Conversely, if the measured distance is less than the desired distance, the ET tube may be withdrawn relative to the measuring device until the desired distance between the expandable stopper and distal tip of the ET tube is achieved.

Positioning an ET Tube During Intubation

The measuring devices described here with alignment and displacement markings on an outer shaft may be used during intubation to facilitate placement of an ET tube a desired distance (e.g., 2-5 cm) from the carina. In this case, the measuring device may be inserted into the ET tube lumen before the ET tube is inserted into a patient's airway, and the ET tube and measuring device may be advanced together through a patient's mouth, past to the vocal cords, and into the trachea. Alternatively, the ET tube may be positioned in a patient's airway first and the measuring device then inserted into the ET tube lumen. After the measuring device and ET tube are in a patient's airway, the measuring device may be aligned with the ET tube, as was described in more detail above, such that the expandable stopper is at the distal tip of the ET tube and in an expanded configuration. The measuring device may then be advanced relative to the ET tube until the expandable stopper engages the carina or until the expandable stopper is positioned a desired distance from the distal tip of the ET tube (e.g., 2-5 cm). In variations where the expandable stopper engages the carina, the distance between the expandable stopper and the carina may then be measured, and the ET tube may be repositioned if necessary (as was described in detail above). In variations where the expandable stopper is positioned a desired distance from the distal tip of the ET tube before the expandable stopper engages the carina, the measuring device and the ET tube may be advanced together until the expandable stopper engages the carina, as was described in more detail above.

Figure 16:
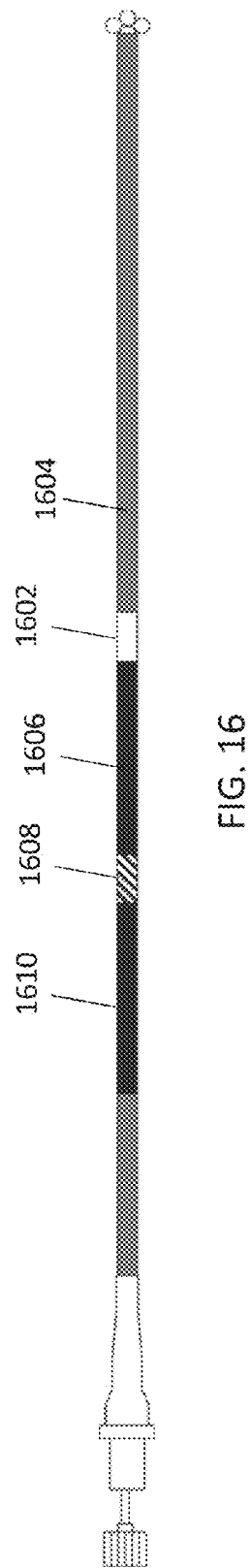
FIG. 16 depicts an illustrative variation of the measuring devices described here.

Variation of Device with an Alignment guide and Colored Regions on the Outer Shaft for Alignment and Measurement As shown in FIG. 16, in another variation of the measuring device, the position markings on the outer shaft (1604) may comprise color and/or patterns. For example, the numerical alignment and displacement markings as described above can be colored differently to denote different longitudinal positions of the outer shaft (1604). The position markings may comprise colored markings that cover longitudinal segments of the outer shaft in regions, supplement the numerical alignment and displacement markings described above, and/or indicate position along the length of the outer shaft in any suitable manner. For example, the colored regions may or may not additionally comprise numerical displacement markers (e.g., 1-cm increments between 1 and 10 cm) that may indicate the distance between the distal tip of the ET tube and the carina during use of the measuring device. While color is one method to differentiate the regions, grey tones, hash markings, texture or any other visual indication may be used. In variations of the measuring device that comprise an alignment sheath, one or more of these regions may be positioned on the alignment sheath.

Variations of the measuring device that comprise colored and/or patterned regions in place of or to supplement numerical displacement and/or alignment markings may be advantageous for ease of use of the device and/or for reducing risk to patients. For example, color or patterns may be interpreted by a user faster and/or more clearly than other variations of markings, which may reduce the time the measuring device is in a patient's airway and/or reduce the risk of a user making an error during alignment and/or measurement.

Position markings configured as longitudinal segments may comprise a distal alignment region (1602) used during initial alignment of the measuring device with the ET tube. The alignment region (1602) may be configured on the outer shaft (1604) such that when it is aligned with one or more specified length markings on an ET tube, the distal end of the outer shaft is aligned with the distal tip of the ET tube. For example, if the alignment region (1602) is positioned 27 cm from the distal end of the outer shaft, aligning this alignment region with a 27 cm length marking on an ET tube may also align the distal end of the outer shaft (1604) with the distal tip of the ET tube.

Position markings configured as longitudinal segments may also comprise a medial, safe displacement region (1608) used for indicating proper positioning of the ET tube relative to the carina (e.g., between 2 cm and 5 cm) and/or proximal and distal, danger displacement regions (1610 and 1606 respectively) used for indicating that the ET tube is positioned farther from or closer to the carina than may be desired. In some instances, the proximal and distal displacement regions (1610 and 1606 respectively) may be the same color, but in other instances they may be different colors. For example, the distal displacement region (1606) may be red, indicating that the user should pull the ET tube out of the mouth to achieve the desired separation distance, and the proximal displacement region (1610) may be yellow, indicating that the user should advance the ET tube with caution to achieve the desired separation distance. However, any combination of colored markings may be used.

In one example, the outer shaft (1604) may comprise a distal, white alignment region (1602) that is 0.5-2 cm in length; a distal, yellow danger region (1606) that is 2-4 cm in length; a medial, green safe region (1608) that is 0.1-3 cm in length; and a proximal, yellow danger region (1610) that is at least 1 cm in length and may extend to the proximal end of the outer shaft (1604). In one particular example, the distal, white alignment region may be 0.5 cm in length; the distal, yellow danger region may be 4 cm in length; the medial, green safe region may be 1 cm in length; and the proximal, yellow danger region may be at least 1 cm in length. In another particular example, the distal, white alignment region may be 1.4 cm in length; the distal, yellow danger region may be 2.4 cm in length; the medial, green safe region may be 1.6 cm in length; and the proximal, yellow danger region may be 5 cm in length. However, the position markings may be of any suitable length and located along the outer shaft (1604) in any suitable manner.

As shown in FIGS. 17A-17C, in some variations, the measuring device may comprise an elongate member (1700) and an alignment guide (1720). The elongate member may comprise an inner shaft with an expandable stopper positioned at a distal end of the inner shaft, an outer shaft comprising a lumen through which a portion of the inner shaft may be slidably disposed, and a plurality of position markings. As described with respect to FIGS. 17A-17C and FIGS. 18A-18C, the expandable stopper of the inner shaft comprises a plurality of prongs and the plurality of position markings comprises alignment and displacement regions. However, it should be appreciated that any of the variations of inner shaft, expandable stopper, outer shaft, and position markings described herein may apply to an elongate member of a measuring device.

The alignment guide (1720) may couple to an external surface of the ET tube (1702) surrounding the outer shaft (1704). For example, FIG. 17B illustrates the alignment guide (1720) being coupled to an ET tube (1702). The alignment guide (1720) may additionally or alternatively couple to an internal surface of the ET tube. The alignment guide (1720) may be temporarily or permanently attached to the ET tube in any suitable manner, such as through a snap fit, adhesive, or bonding. In some variations of the measuring device, as is seen in FIG. 17A, the alignment guide (1720) may also be attached to the elongate member (1700) when the alignment guide is not coupled to the ET tube (1702) (e.g., when the elongate member and clip are packaged, for storage of the clip).

The alignment guide (1720) may comprise a marking indicator or positioning area that may be aligned with one or more position markings. For example, as shown in FIGS. 17A-17C, the marking indicator or positioning area may comprise a viewfinder (1722) (e.g., translucent or transparent window, opening) through which at least a portion of one or more alignment markings, displacement markings, and/or colored regions are visible. The size of the viewfinder (1722) may range from 0.25 cm to 2 cm in length. In one variation, the size of the viewfinder may be 1 cm in length. As the outer shaft (1704) is displaced through the lumen of the ET tube, colored regions and/or any numerical alignment or displacement markings may be displayed through the viewfinder (1722). The viewfinder window or opening may be fully bound around its perimeter, or partially bound.

The alignment guide (1720) may comprise indicia (e.g., numerical, symbolic, other suitable markings) to indicate the longitudinal position on the ET tube where the alignment guide (1720) may be coupled. For example, as is shown in FIGS. 17A-17C, the alignment guide (1720) may be marked with "26" and "27" to indicate that the alignment guide should be coupled to the ET tube between the 26 cm and 27 cm length markings on the ET tube. However, the alignment guide may comprise any suitable indicia.

Measurement Methods

Figure 18A:
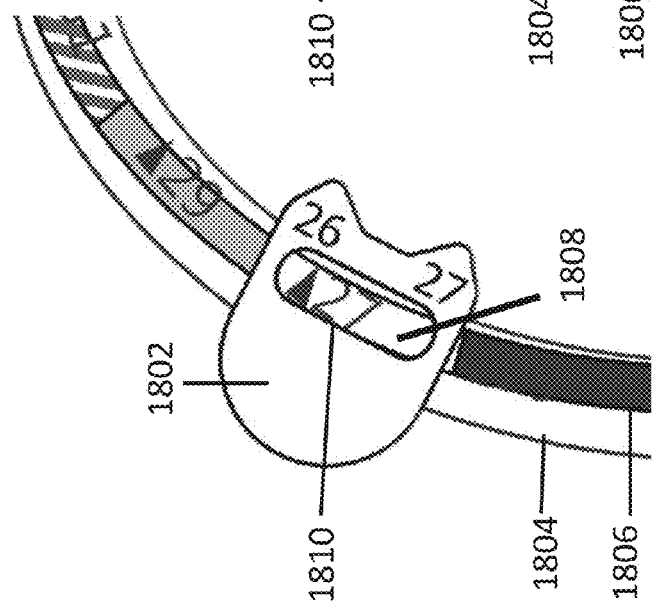
FIGS. 18A-18C depict a portion of a method of using an alignment guide of the measuring devices described here to measure a distance in an airway of an intubated patient.
Figure 18B:
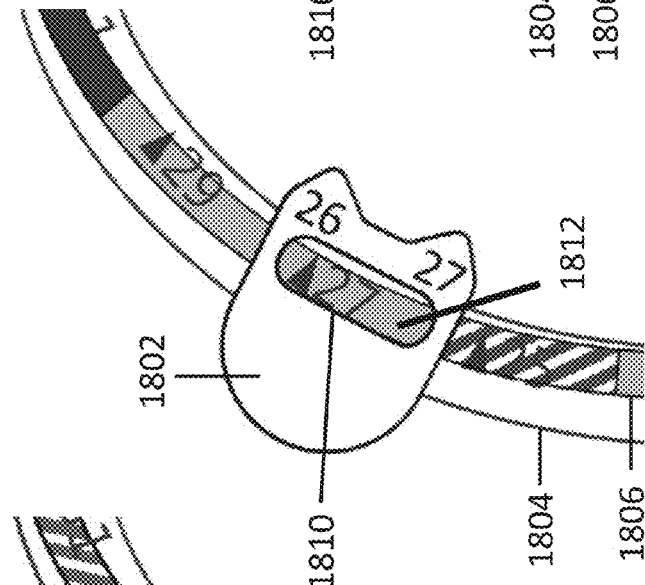
Figure 18C:
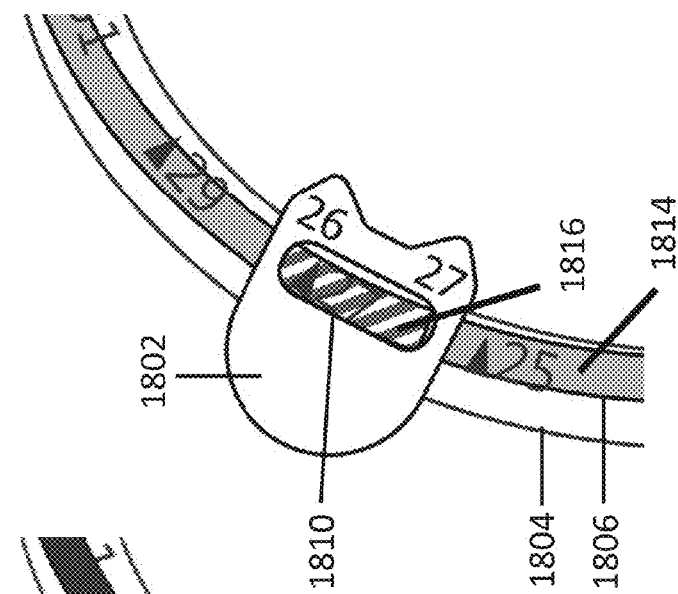

A variation of the measuring device comprising an alignment guide and colored regions on an elongate member may be used in methods for determining a position of an ET tube within an intubated patient and/or positioning an ET tube within a patient, as is illustrated in FIGS. 18A-18C. In these and other suitable applications, the user may couple the alignment guide (1802) onto the ET tube (1804), such that the alignment guide is configured to surround the ET tube and the outer shaft (1806) when the elongate member is inserted into the ET tube. Methods for introduction of the elongate member into an ET tube may be the same as were described in more detail for the variations of measurement devices described above.

Alignment

The elongate member may be advanced until the alignment marking on the outer shaft is aligned with the marking indicator of the alignment guide. In variations of the alignment guide comprising a viewfinder and an alignment region, as is shown in FIG. 18A, the elongate member may be advanced until the alignment region (1808) on the outer shaft (1806) is visible in the viewfinder (1810) of the alignment guide (1802). This may indicate that the distal end of the elongate member is aligned with the distal tip of the ET tube, as was described in more detail above.

Measurement

With the expandable stopper in the expanded configuration, the elongate member may be advanced relative to the ET tube. When there is resistance to further advancement of the elongate member, the expandable stopper may have engaged the carina. The user may then observe one or more colored regions on the outer shaft (1806) through the viewfinder (1810) on the alignment guide (1802). Depending on the color viewed through the viewfinder (1810), the user may determine if the ET tube is positioned at a desirable separation distance from the carina (e.g., 2-5 cm from the distal tip of the ET tube to the carina) or if the ET tube may need to be repositioned. As shown in FIG. 18B, if the proximal, danger displacement region (1812) is visible in the viewfinder (1810) of the alignment guide (1802), then the ET tube may be farther from the carina than the desired position, and the ET tube may need to be advanced, as was described in more detail above. Similarly, if the distal, danger displacement region (1814) is visible in the viewfinder (1810) of the alignment guide (1802), then the ET tube may be closer to the carina than the desired location. However, as shown in FIG. 18C, if the medial, safe displacement region (1816) is visible in the viewfinder (1810) of the alignment guide (1802), then the ET tube may located at the desired location.

While the viewfinder (1810) is shown in FIGS. 18A-18C as being 1 cm in length, in one embodiment, the viewfinder may be 0.5 cm in length. In a variation where the viewfinder is 0.5 cm, if the medial, safe displacement region is visible in any portion of the viewfinder, the ET tube may be located in the desired position.

ET Tube Positioning

The measuring devices described here comprising colored and/or patterned regions and/or an alignment guide may be used to help position an ET tube relative to tissue. In some instances, the measuring device may be used to reposition an ET tube after the patient has been intubated. In other instances, the measuring device may be used during intubation of a patient (e.g., to help prevent the ET tube from being advanced past the carina during intubation and/or to position the ET tube a predetermined distances from the carina).

Repositioning an ET tube

In order to reposition an ET tube using the measuring device described here, the distance between a distal tip of an ET tube and the carina of a patient may first be measured using the methods described above. If a proximal or distal, danger displacement region (1812 and 1814 respectively) is visible in the viewfinder (1810), a user may reposition the ET tube (1804). Repositioning the ET tube may be done by advancing (if the proximal danger region is seen) or retracting (if the distal danger region has seen) the ET tube relative to the elongate member until the medial safe region (1816) is visualized in the viewfinder (1810). Repositioning of the ET tube may be done with the alignment guide (1802) still coupled to the ET tube.

Positioning an ET Tube During Intubation

A measuring device comprising colored and/or patterned regions and/or an alignment guide may also be used for positioning an ET tube in a desired location (e.g., 2-5 cm from the carina) during intubation. In this case, the alignment guide (1802) may be coupled to the ET tube (1804) before or after the ET tube is inserted into a patient's airway. The alignment guide (1802) is coupled to the ET tube (1804) at a predetermined location, such as by aligning indicia on the alignment guide with corresponding length markings on the ET tube, as was discussed in more detail above. The elongate member may be inserted into the ET tube lumen before the ET tube (1804) is inserted into a patient's airway, and the ET tube and elongate member may be advanced together through a patient's mouth, past the vocal cords, and into the trachea. Alternatively, the ET tube may be positioned in a patient's airway first and the elongate member then inserted into the ET tube lumen.

After the elongate member and ET tube (1804) are in a patient's airway, the elongate member may be aligned with the ET tube, as was described in more detail above, such that the expandable stopper may be at the distal tip of the ET tube (1804) and in an expanded configuration. The elongate member may then be advanced relative to the ET tube until the expandable stopper engages the carina or until the expandable stopper is positioned a desired distance from the distal tip of the ET tube, as indicated by the medial safe region (1816) being visible in the viewfinder (1810) of the alignment guide (1802). In variations where the expandable stopper engages the carina, a colored region may be visible in the viewfinder of the alignment guide. As was described in detail above, if a proximal or distal danger region (1812 and 1814 respectively) is visible in the viewfinder (1810), a user may reposition the ET tube (1804). If the medial safe region (1816) is present in the viewfinder (1810), the ET tube (1804) may not need to be repositioned. In variations where the expandable stopper is positioned a desired distance from the distal tip of the ET tube (1804) before the expandable stopper engages the carina, the elongate member and the ET tube may be advanced together until the expandable stopper engages the carina.

Removal of Device

For any of the measuring devices described here, once the distance between the carina (CA) and the distal tip of the ET tube has been measured, the ET tube may be repositioned if desired, and the measuring device may be removed from the body. To remove the measuring device from the body, the inner shaft and the outer shaft may be withdrawn through the ET tube and any connectors. In variations where the outer shaft is temporarily connected to the ET tube (e.g., by a securement mechanism), the outer shaft may be decoupled prior to or during withdrawal of the outer shaft. Additionally, in some variations, the expandable stopper may be returned to a low-profile configuration prior to removal. For example, in some variations the inner shaft may be withdrawn relative to the outer shaft to pull the expandable stopper at least partially into the lumen of the outer shaft, which may constrain the expandable stopper to a low-profile configuration within the lumen. In other variations, the expandable stopper may remain exposed from the outer shaft during withdrawal of the measuring device. In some instances, this may cause the expandable stopper to drag across or otherwise contact an interior of the ET tube, which may scrape material from or otherwise clean the interior of the ET tube. In variations of the measuring devices comprising an alignment guide, the alignment guide may be decoupled from the ET tube when it is not being used for measurement. In some variations, the alignment guide may remain attached to an ET tube between measurements.

Frequency of Measurement

The measuring devices described here may be used to measure the ET tube position on a scheduled or repeated basis. In some variations, the distance between the distal tip of the ET tube and the carina may be measured according to a schedule (e.g., one or more times daily, in lieu of daily chest x-rays to check ET tube positioning, one or more times weekly). Additionally or alternatively, the separation distance may be measured after patient movement. For example, the separation distance may be measured when a patient is moved from one location (e.g., from one bed to another, or one room to another), after a patient is repositioned on a bed (e.g., by one or more orderlies or health care practitioners), and/or after other patient movement (e.g., shifting or thrashing by the patient).

Determining if the ET Tube or Measuring Device is Distal to the Carina

In some instances, the distal tip of an ET tube may be positioned distal to the carina and in one of the main bronchi. In these instances, the expandable stopper may be unable to engage the carina, as the distal end of the inner shaft (in variations comprising an inner and outer shaft) or elongate shaft (in variations comprising only one shaft) may exit the ET tube distal to the carina. In this scenario, the distal end of the measuring device may catch on the first bifurcation of a main bronchus, which is approximately 1.5-2.5 cm past the carina in the right main bronchus and 3-4 cm past the carina in the left main bronchus. Most often, if an ET tube distal tip is positioned in a main bronchus, it is in the right main bronchus because of the orientation and size of the right main bronchus compared to the left main bronchus. Accordingly, it may be desirable for a user to determine if the ET tube is positioned distal to the carina in the right main bronchus.

For example, in some variations, a medial, safe displacement region of a measuring device may be configured such that when it is aligned with a marking indicator of an alignment guide coupled to an ET tube, the expandable stopper may be 3-4 cm from the distal tip of the ET tube. If the distal tip of the ET tube is inserted into the right main bronchus and the expandable stopper engages the bifurcation of the right main bronchus when advanced, positioning the ET tube according to the methods described in detail herein may comprise withdrawal of the ET tube proximally until the medial, safe displacement region is aligned with the marking indicator. This may position the distal tip of the ET tube 0.5-2.5 cm proximal to the carina (3-4 cm proximal to the bifurcation of the right main bronchus). If the position of the ET tube is then measured a second time, the expandable stopper may now engage the carina, and the relationship of the displacement markings and marking indicator may indicate that the ET tube may need to be withdrawn proximally again to position the distal tip of the ET tube 3-4 cm proximal to the carina. In some variations of the methods, if a first measurement indicates that the ET tube may need to be withdrawn proximally, the ET tube may be withdrawn as described above. The ET tube position may then be measured a second time. If the second measurement indicates that the ET tube may need to be withdrawn a second time, the ET tube may have been positioned in the right main bronchus prior to the first measurement.

In other variations, the measuring device may comprise a guiding system that may indicate if the distal end of the measuring device is positioned to the left or the right of a center line of the patient. If the guiding system indicates the distal end of the measuring device is to the left or right of the center line, a user may determine that the measuring device is positioned past the carina in one of the main bronchi. In some variations, the measuring device may comprise a magnetic member that may be tracked by an external sensor. In other variations, the measuring device may comprise a light source that may be viewed externally of the patient. In still other variations, the measuring device may comprise a receiver that is capable of detecting or otherwise recording a heartbeat, such that the intensity of the detected heartbeat indicates a distance from the heart. For example, if the detected heartbeat gets fainter, a user may determine that the measuring device has moved past the carina.

In still other variations, the measuring device may be configured to determine a diameter of the portion of the airway in which the measuring device is positioned. A user may use this diameter measurement to determine whether the measuring device is positioned in the larger trachea or one of the smaller bronchi. The diameter may be measured using a mechanical expander, a sound wave generator, an electromagnetic source, or the like.

In some instances, airflow through a patient's airway may be used to determine if a measuring device has been positioned past the carina. For example, in some variations the measuring device may have an occluding member (such as an inflatable balloon) at or near the distal end of the measuring device. The occluding member may be inflated to occlude the airway and block airflow therethrough. If the measuring device is positioned in the trachea, the balloon will occlude the trachea and ventilator airflow resistance may increase significantly. Conversely, if the measuring device is positioned in one of the main bronchi, the balloon will only occlude that bronchus, and the ventilator airflow resistance will not increase as much (since air may still flow through the trachea into the other bronchus).

Determining if the ET Tube or Measuring Device is in the Esophagus

In some instances, during intubation, the distal tip of an ET tube may be positioned in the esophagus instead of the trachea. In these instances, the expandable stopper may be unable to engage the carina as the distal end of the inner shaft (in variations comprising an inner and outer shaft) or elongate shaft (in variations comprising only one shaft) will not encounter a bifurcation during advancement. Accordingly, it may be desirable for a user to determine if the ET tube is positioned in the esophagus. For example, in some variations, advancement of the measuring device (e.g. inner shaft, elongate shaft, inner and outer shaft) more than a certain distance without encountering resistance (e.g., by a bifurcation of the airway) may indicate that the ET tube has been positioned in the esophagus. For example, if the ET tube is positioned in the esophagus, the measuring device may be advanced at least 15 cm beyond the distal tip of the ET tube before meeting resistance when engaging the lower esophageal sphincter. The average adult trachea is about 10-13 cm in length, so if the ET tube is positioned in the trachea, the distance a measuring device may be advanced beyond the distal tip of the ET tube before encountering resistance may be less than 13 cm. Accordingly, advancement of the measuring device 15 cm or more beyond the distal tip of an ET tube without encountering resistance may indicate that the ET tube may be positioned in the esophagus.

The invention claimed is:

1. A measuring device for measuring a distance in an airway of a patient intubated with an endotracheal tube, comprising:
an elongate member configured to be removably inserted through an endotracheal tube, comprising:
an inner shaft, wherein the inner shaft comprises an expandable stopper positioned at a distal end of the inner shaft, the expandable stopper moveable between a low-profile configuration and an expanded configuration, and wherein the expandable stopper comprises a plurality of prongs;
an outer shaft comprising a lumen extending therethrough, wherein the inner shaft is slidably disposed in the lumen of the outer shaft; and
a plurality of position markings located on the outer shaft; and
an alignment guide comprising a marking indicator and position indicia, wherein the alignment guide is configured to removably attach to a predetermined portion of an external surface of the endotracheal tube and wherein the position indicia depicts a distance, from a distal end of the endotracheal tube, where the predetermined portion is located, the marking indicator is configured, in use, to determine the position of the endotracheal tube using the plurality of position markings on the outer shaft; and
wherein one of the plurality of position markings is an alignment marking located on the outer shaft at a distance, from a distal end of the elongate member, indicated by the position indicia of the alignment guide, and at least one of the plurality of position markings is a displacement marking located on the outer shaft 2 cm to 5 cm proximal to the alignment marking.

2. The device of claim 1, wherein the marking indicator comprises a viewfinder.

3. The device of claim 1, wherein the plurality of position markings comprises a proximal displacement region having a first color, a distal displacement region having a second color, and a medial displacement region having a third color different from the first and second colors.

4. The device of claim 3, wherein the medial displacement region is configured such that when aligned with the marking indicator, the expandable stopper is at a predetermined distance from the distal tip of the endotracheal tube.

5. The device of claim 4, wherein the predetermined distance is within 2-5 cm.

6. The device of claim 3, wherein the first and second colors are the same.

7. The device of claim 3, wherein the first and second colors are different.

8. The device of claim 1, wherein the alignment marking comprises a region having a color.

9. The device of claim 1, wherein the plurality of prongs comprises at least 5 prongs.

10. The device of claim 1, wherein the plurality of prongs comprise prongs of different lengths.

11. The device of claim 1, wherein one or more prongs of the plurality of prongs comprise one or more curves.

12. The device of claim 11, wherein when the expandable stopper is in the expanded configuration, one or more prongs of the plurality of prongs comprise a curved proximal portion that forms an angle with a surface parallel to a longitudinal axis of the device that is less than 75 degrees.

13. The device of claim 11, wherein when the expandable stopper is in the expanded configuration, one or more prongs of the plurality of prongs comprise a curved distal portion that forms an angle with a surface parallel to a longitudinal axis of the device that is between 1 and 45 degrees.

14. The device of claim 1, wherein the plurality of prongs comprises atraumatic tips.

15. The device of claim 14, wherein the atraumatic tips comprise ball tips.

16. The device of claim 15, wherein the ball tips have a diameter of 0.065-0.085.

17. The device of claim 1, wherein the outer shaft comprises a flared distal portion and a middle portion, and wherein a maximum transverse dimension of the flared distal portion is in the range of 4.5-6 millimeters and a maximum transverse dimension of the middle portion is in the range of 2-4 millimeters.

18. The device of claim 1, wherein the plurality of prongs is configured to deflect with less than 0.2 lbf force.

* * * * *